United States Patent
Hirabayashi et al.

(10) Patent No.: US 6,579,714 B1
(45) Date of Patent: Jun. 17, 2003

(54) METHOD OF CULTURING ALGAE CAPABLE OF PRODUCING PHOTOTROPHIC PIGMENTS, HIGHLY UNSATURATED FATTY ACIDS, OR POLYSACCHARIDES AT HIGH CONCENTRATION

(75) Inventors: Seishiro Hirabayashi, Kula, HI (US); Alexander Prilutsky, Beer Sheva (IL); Hisato Sadamatsu, Kawasaki (JP)

(73) Assignee: Micro Gaia Co., Ltd., Toyama-ken (JP)

( * ) Notice: Subject to any disclaimer, the term of this patent is extended or adjusted under 35 U.S.C. 154(b) by 20 days.

(21) Appl. No.: 09/831,905

(22) PCT Filed: Sep. 26, 2000

(86) PCT No.: PCT/JP00/06611
§ 371 (c)(1),
(2), (4) Date: Feb. 1, 2002

(87) PCT Pub. No.: WO01/23519
PCT Pub. Date: Apr. 5, 2001

(30) Foreign Application Priority Data

Sep. 29, 1999 (JP) .......................... 11-277611

(51) Int. Cl.[7] .............................. C12N 1/12; C12M 1/04
(52) U.S. Cl. .................. 435/292.1; 435/101; 435/134; 435/257.1; 435/257.3; 47/1.4
(58) Field of Search .......................... 435/292.1, 296.1, 435/257.1, 257.3, 101, 134; 47/1.4; 210/220; 261/121.1, 123, 124; 239/722, 754, 263, 264, 229, 233

(56) References Cited

U.S. PATENT DOCUMENTS

| | | | |
|---|---|---|---|
| 3,224,143 A | * 12/1965 | Tew et al. | |
| 4,320,594 A | 3/1982 | Raymond | 47/1.4 |
| 4,324,068 A | * 4/1982 | Anthony | 47/1.4 |
| 4,952,511 A | * 8/1990 | Radmer | 362/340 |
| 5,137,828 A | 8/1992 | Robinson et al. | 435/296 |
| 5,534,417 A | * 7/1996 | Arad et al. | 435/257.1 |
| 5,958,761 A | * 9/1999 | Yogev et al. | 435/257.1 |
| 6,348,347 B1 | * 2/2002 | Hirabayashi et al. | 239/229 |

FOREIGN PATENT DOCUMENTS

| | | | |
|---|---|---|---|
| EP | 0 999 265 A1 | | 5/2000 |
| GB | 1 547 373 | | 6/1979 |
| JP | 08-38154 A | * | 2/1996 |
| JP | 08-38155 A | * | 2/1996 |
| JP | 08-038156 A | * | 2/1996 |
| JP | 08-116960 A | * | 5/1996 |

OTHER PUBLICATIONS

Tanishita. "Atarashii Reactor ni yoru Sourui Kougousei no Kouritsuka." Bio Engineering (1992), vol. 9, No. 9, pp. 585–590.*

Gudin et al. "Solar Biotechnology Study and Development of Tubular Solar Receptors for Controlled Production of Photosynthetic Cellular Biomass for Methane Production and Specific Cellular Biomass", Energy Biomass (1984), pp. 184–193.*

* cited by examiner

*Primary Examiner*—William H. Beisner
(74) *Attorney, Agent, or Firm*—Armstrong, Westerman & Hattori, LLP

(57) ABSTRACT

The present invention relates to a method for cultivation and manufacturing efficiently algae containing useful substances in cells thereof in a high concentration. According to conventional cultivation apparatus, shear stress applied to algae causes difficulty of high density cultivation; however, by cultivation of algae by using a convenient cultivation apparatus having a dome shape, conical shape, or cylindrical shape and made by a clear material, high density cultivation has been realized without shear stress. The present cultivation apparatus realizes more efficient cultivation in combined use with a separate gas discharging apparatus. In addition, the present invention can be applied to a wide variety of algal species having ability to produce highly unsaturated fatty acid, a photosynthetic pigment, or a polysaccharide.

11 Claims, 13 Drawing Sheets

METHOD OF CULTURING ALGAE CAPABLE OF PRODUCING PHOTOTROPHIC PIGMENTS, HIGHLY UNSATURATED FATTY ACIDS, OR POLYSACCHARIDES AT HIGH CONCENTRATION

TECHNICAL FIELD

The present invention relates to a method for culturing algae having an ability of producing highly unsaturated fatty acids, photosynthetic pigments, and/or polysaccharides to manufacture the algae containing these substances in algal cells, more specifically relates to the method for culturing algae having an ability of producing the highly unsaturated fatty acids, the photosynthetic pigments, and/or the polysaccharides in a culture medium under light irradiation and/or aeration condition to manufacture efficiently algae containing these highly unsaturated fatty acids, photosynthetic pigments, and/or polysaccharides in algal cells in a high concentration using a certain cultivation apparatus.

BACKGROUND ART

Development of a cultivation method for algae, wildly growing, is needed for stable, high yield production of the photosynthetic pigment used as a safe feed for a cultured fish and as a safe food additive and unsaturated fatty acid, photosynthetic pigment, and/or polysaccharide used for a medical drug and a health food. However, cultivation method has been limited to a few numbers and thus, very limited species such as Chlorella and Spirulina were studied and a method for an efficient cultivation is has not been yet established.

Algae perform biosynthesis of a useful substance by photosynthesis through absorption of carbon dioxide. In addition, it is important that algal cultivation is carried out efficiently and therefore, an apparatus for cultivation is necessary for efficient photosynthesis. Hence, improving the apparatus for cultivation and developing a new apparatus for cultivation are being conducted.

So far, as the apparatus for cultivation for algae, for example, a cultivation pond, a raceway type cultivation apparatus, a tubular type cultivation apparatus, a liquid membrane-forming cultivation apparatus have been well known. In the cultivation pond, a concrete-made cultivation pond or cultivation vessel are prepared in the outdoors to build up a pond in which a culture solution is filled and a species of a microalgae exemplified by Chlorella is cultured in the pond using sunlight. However, this type of the cultivation apparatus requires such area as 3000 $m^2$ for the pond resulting in a huge volume.

In addition, cultivation of microalgae by using the cultivation apparatus of this type causes a high concentration of algal cells containing in the culture solution according to progress of cultivation resulting in thick green coloration of the culture solution to disturb reaching of sunlight to a bottom of the pond. From such phenomenon, the following problem comes up: unless algal cell density necessary for cultivation is reduced, a total algal photosynthetic efficiency is lowered.

Consequently, a depth of the pond must be set to 15 cm or smaller and a land for mass cultivation of algal cells must be vast. Further, a concentration of the culture solution cannot be made higher and thus, in collection of a culture from the solution, the following problem comes up: the culture must be collected from a huge amount of a low density culture solution.

On the other hand, the cultivation pond must be stirred to make algal photosynthesis easy. However, a large amount of energy is required for stirring the huge volume of the low concentration liquid. In addition, the cultivation pond is located in the outdoors and in an opened state and hence, such exogenous matters as dust and waste are easy to contaminate the liquid and airborne microorganisms and cells of other species of microalgae contaminate the pond to propagate resulting in the following problem: culture of a high purity and a high quality cannot be yielded.

The cultivation pond is located in the outdoors and thus, a temperature thereof changes according to a change of weather to cause very difficulty to maintain the temperature of the pond in a constant value. Particularly, there is a defect that in winter in a certain locality, the temperature drops excessively.

Caused by such status, cultivation of algae by using the cultivation pond cannot be applicable to other algal genera than Chlorella, Spirulina, and Dunaliella, which can grow under a unique condition such as a high pH and a high salinity.

The raceway type cultivation apparatus has a circulatory path, for culture solution, made by partitioning of an inside of the cultivation vessel with a straightening vane and is used for cultivation of algae by the method by which the culture solution is circulated in this circulatory path by using means for circulation. This system is of an improved circulation system of the culture solution and a photosynthetic rate of algae lowers, similar to the cultivation method using the cultivation pond, according to progress of cultivation and therefore, does not allow efficient use of light energy. Consequently, the following problem also comes up: an efficiency of carbon dioxide is low. In order to achieve efficient use of light, irradiation of sunlight to the liquid through an optical fiber has been proposed (Japanese Utility Model Application Laid-Open No. 5-43900).

In operating algal cultivation by using this system, the liquid is circulated by mechanical stirring and thus, the following inevitable defects occur: algal cells are broken and a shear stress occurs (a phenomenon in which algal cells are cut by a shear stress to cause reduction of cellular activity resulting in a low propagation rate).

The tubular type cultivation apparatus is the apparatus for algal cultivation by using the cultivation apparatus comprising a light transmission tube. Algal cultivation by using this apparatus allows no contamination of the culture solution by non-objective bacteria and making culture concentration high and thus, is a very beneficial method for collection of the useful substance, which is produced by algae, by separating algae from the culture solution.

However, after long-time algal cultivation, algae attach to an internal wall of the tube to disturb light pass through the tube very. These facts make efficient algal cultivation difficult and also make removal of algae attached to the internal wall of the tube difficult.

In order to solve these problems, the following method has been proposed: a cleaning ball is put in the tube an the ball is always circulated together with the culture solution to clean the internal wall of the tube (Japanese Patent Application Laid-Open No. 6-90739). However, even by this method, the following and other many problems remain: dirt and algal attachment of the internal wall of the tube cannot be continuously removed completely, the ball must be collected to clean and also, the ball must be always circulated in the tube. In addition, a further problem of this system for algal cultivation is that cultivation operated inside the tube allows oxygen gas, which is generated by algal photosynthesis to stay, in the tube and oxygen inhibits algal photosynthesis. Based on these facts, a device of the apparatus has been proposed to suppress a bad effect caused by oxygen, generated by photosynthesis, on cultivation (Japanese Patent Application Laid-Open No. 9-121835).

In the liquid membrane-forming cultivation apparatus, a dome-shaped, light-passing lid body is installed on an top face of the cultivation vessel and culture solution is jetted from a bottom to an internal face of an apical part of the dome-shaped lid body to form a liquid membrane on the internal face of the lid body and irradiate a light on this liquid membrane (Japanese Patent Application Laid-Open No. 8-38159).

However, there are problems: this system proposed requires a circulation pump for continuation of formation of the liquid membrane, is not suitable for mass cultivation, and does not allow using sunlight.

A panel type cultivation apparatus is used for algal cultivation by installing a thin box-like apparatus, which is prepared by using two resin-made panel boards, with inclination.

This apparatus itself is a closed type similar to the tubular type cultivation apparatus, for example, and has an advantage of no contamination of the culture solution by bacteria and wastes. However, the following problem come up: oxygen gas generated according to progress of cultivation dissolves in the culture solution and stays in the apparatus to inhibit algal photosynthesis.

In addition, in the case where the apparatus is installed in the outside, an altitude of the sun and a sunlight incident angle to a surface of the apparatus change according to time from sunrise to sunset to cause an insufficient total amount of sunlight received per an area, where it has been installed.

Japanese Patent Application Laid-Open No. 10-304867 discloses the method for designing conveniently the panel type cultivation apparatus having a most suitable light environment. In the disclosure, by combination of a relation between a passed light amount and a matter production activity with the relation between the passed light amount and the light path length of a reactor, the method for designing conveniently the light path length of the cultivation apparatus was created and the cultivation apparatus designed by this method was proposed.

However, the above described principal problems have not been solved.

Algae accumulate useful substances in their bodies by photosynthesis and the most important subject is efficient algal photosynthesis as possible. A factor for efficient photosynthesis may be increase in a light-receiving area of the cultivation apparatus, efficient stirring of the culture solution, adjusting a thickness or a depth of the culture solution, easy removal and cleaning of algal cells attached to the internal surface of the cultivation apparatus, temperature regulation, prevention of contamination of bacteria, cells of other algal species, and waste.

The problem of the light-receiving area is influenced by the larger light-receiving area as possible and efficient irradiation of the light on the culture solution.

For example, in the cultivation vessel and the cultivation pond, the surface area thereof is determined by the surfaces of the cultivation vessel and the cultivation pond and hence, in order to increase the surface area, increase in a size of the vessel and pond is an only one way to achieve it and there is no other way.

Stirring the culture solution is essential for even irradiation of the light on the cultivation pond and normally, means thereof are frequently by stirring or moving the liquid by using the pump and mechanical stirring in the vessel and pond.

However, such mechanical stirring causes break of and the shear stress to algal cells resulting in bad effects.

The photosynthesis rate differs between algal species and therefore, for species having a low rate and fast rate, the depth of the culture solution must be changed and the depth must be changed according to the objective culture concentration. As described above, the thickness or depth of the culture solution must be freely adjusted according to such conditions as algal species and the objective culture concentration.

Removal and cleaning of algae attached to the internal surface of the cultivation apparatus can be normally carried out in the outdoor open type cultivation pond and cultivation vessel. However, In the closed type cultivation apparatus, attached algae do not allow the light to pass and thus, removal and cleaning of algae must be carried out. Subsequently, at a stage of completion of cultivation, for operation of the next cultivation, the apparatus must be adapted to have a structure by which the internal surface of the cultivation apparatus must be cleaned and attached matter must be readily removed.

Temperature regulation is very important particularly for the closed apparatus to prevent occurrence of cultivation trouble caused by excessive rise of the temperature of the liquid in summer. In order to solve-this problem, the following method is known: cool water is mixed into the culture solution. However, the culture solution is diluted and hence, a huge amount of the culture solution diluted is treated in collection of the culture in the next step. Therefore, this method is very disadvantage for industrial application.

The cultivation apparatus is the apparatus used normally in the outdoors or the apparatus used normally in doors. By this reason, the following problem occurs: when the apparatus for the outdoors is used in doors, efficiency of light use becomes low and on the other hand, another problem occurs: the apparatus for use in doors is not used in the outdoors. The cultivation apparatus with a simple structure is desired to operate cultivation under normal condition cultivation in doors and in the outdoors.

Stirring the culture solution is an essentially necessary operation for even cultivation.

This is because of the following reasons: 1) a difference occurs between cultivation rates of a surface layer part and a deep layer part of the liquid medium, 2) such gas as air and carbon dioxide must be evenly distributed in the liquid medium, in other words, a whole of the culture solution, 3) the light must be evenly distributed in algae for cultivation, 4) prevention of sedimentation of algae readily making a colony during cultivation to stay in the bottom of the liquid and dispersion repeated in the culture solution.

It is required to stir always such culture solution and supply air or carbon dioxide gas to the culture solution. However, such conventional cultivation method has various issues as described above and therefore, is not a sufficient cultivation method.

DISCLOSURE OF THE INVENTION

The present invention improves defects of the conventional cultivation method as described above and has objects to provide the method for algal cultivation in the high yield and at a low cost to produce the photosynthetic pigment used as the safe feed for the cultured fish and ads the safe food additive and the unsaturated fatty acid, or polysaccharide used for a medical drug and the health food and the method for manufacturing algae containing the unsaturated fatty acid, photosynthetic pigment and/or polysaccharide in algal cells in a high concentration efficiently and in a state without contamination by impurities, In order to solve the above described subjects, according to the present invention, the culture medium is filled in a gap and a space made by an internal clear material and an external clear material, air or carbon dioxide gas is injected from the bottom part and the light is irradiated under an aeration condition to make algae photosynthesize for production of the unsaturated fatty acid, photosynthetic pigment and/or polysaccharide in algal cells in a high quantity to manufacture algae containing these substances. Through such steps, high concentration cultivation can be achieved without contamination by algal cells of other species, waste, and bacteria.

The present invention is the method for culturing algae, which has the ability of producing the highly unsaturated fatty acid, the photosynthetic pigment, and/or the polysaccharide, in the high concentration in the culture medium by using the cultivation apparatus under light irradiation and aeration conditions to manufacture the algae containing the highly unsaturated fatty acid, the photosynthetic pigment, and/or the polysaccharide, wherein the above described cultivation apparatus employed is that selected from those with any one shape of the dome shape, conical shape, or cylindrical shape;

the cultivation apparatus with the dome shape comprises an external hemispheric dome made from a clear material, an internal hemispheric dome made from a clear material, and the bottom part connecting bottom end parts of both the domes, and a cylindrical opening member is installed on a top part of the external hemispheric dome and a member for leading air and/or carbon dioxide gas and a discharging member for the culture solution are installed on the bottom part;

the cultivation apparatus with the conical shape comprises an external conical circumferential wall made of the clear material, a clear internal conical circumferential wall, and the bottom part connecting bottom end parts of both the circumferential wall, and a cylindrical opening member is installed on the top part of the external conical circumferential wall and a member for leading air and/or carbon dioxide gas and a discharging member for the culture solution are installed on the bottom part;

or, the cultivation apparatus with the cylindrical shape comprises an external cylindrical circumferential wall made of the clear material and having an upper wall an internal cylindrical circumferential wall having the upper wall made of the clear material, and the bottom part connecting bottom end parts of both the circumferential wall, and the cylindrical opening member is installed on a central part of the upper wall of the external cylindrical circumferential wall and a member for leading air and/or carbon dioxide gas and a discharging member for the culture solution are installed on the bottom part.

In addition, the method for culturing algae, which has the ability of producing the highly unsaturated fatty acid, the photosynthetic pigment, and/or the polysaccharide, in the high concentration in the culture medium by using the cultivation apparatus under light irradiation and aeration conditions to manufacture the algae containing the highly unsaturated fatty acid, the photosynthetic pigment and/or the polysaccharide, wherein the above described cultivation apparatus used is the apparatus comprises a main body of the cultivation apparatus and a gas discharging apparatus; and the main body of the cultivation apparatus is the cultivation apparatus with the dome shape, conical shape, or cylindrical shape, wherein the cultivation apparatus with the dome shape comprises the external hemispheric dome made from a clear material, the internal hemispheric dome made from the clear material, and the bottom part connecting bottom end parts of both the domes, and a cylindrical opening member is installed on the top part of the external hemispheric dome and a discharging member for the culture solution is installed on the bottom part;

the cultivation apparatus with the conical shape comprises the external conical circumferential wall made of the clear material, the internal conical circumferential wall made from the cleat material, and the bottom part connecting bottom end parts of both the circumferential wall, and a cylindrical opening member is installed on the top part of the external conical circumferential wall and a discharging member for the culture solution is installed on the bottom part;

or, the cultivation apparatus with the cylindrical shape comprises the external cylindrical circumferential wall having the upper wall made of the clear material, the internal cylindrical circumferential wall having the upper wall made of the clear material, and the bottom part connecting bottom end parts of both the circumferential wall, and a cylindrical opening member is installed on the central part of the upper wall of the external cylindrical circumferential wall and a discharging member for the culture solution is installed on the bottom part;

the gas discharging apparatus is configured by opposite two square base board, a bubble leading member, of which section has a square shape lacking a side or a reversed U-shape, opened downward, and a discharge nozzle, the bubble leading member is installed with inclination to an upper side face of the square base board, forms the upper wall made by extending an inclined wall of the upper face of the bubble leading member by bending almost horizontally in the upper end part, and has a side wall extending from both the side ends of the inclined wall and the upper wall, and each of the bottom end parts of both the side walls are jointed on the two upper side faces of the square base board, and the discharge nozzle is rotatably attached through a via hole made in the bottom part of the inclined wall.

Further, the method using the cultivation apparatus, wherein the clear material is any one selected from an acrylic resin, polycarbonate, polypropylene, polyethylene, and polyvinyl chloride.

According to the above described cultivation apparatus, with a purpose of controlling a temperature of the culture solution, a water spraying member and a water spray receiving member may be installed in the outside of the cylindrical opening member arid an outer circumference of the bottom part, respectively and in addition, an artificial light source may be installed in spaces of the internal hemispheric dome, the internal conical circumferential wall, or the internal cylindrical circumferential wall.

The cultivation apparatus for algae, used in the present invention, is the cultivation apparatus for algae described in an international patent application (PCT/JP99/01585) and is that described below.

The apparatus used for cultivation according to the present invention will be described below.

The cultivation apparatus for algae, used in the present invention, is the cultivation apparatus with the dome shape selected from those with any one shape of the dome shape, conical shape, or cylindrical shape, wherein the cultivation apparatus with the dome shape comprises the external hemispheric dome made from the clear material, the internal hemispheric dome made from the clear material, and the bottom part connecting bottom end parts of both the domes, and the cylindrical opening member is installed on the top part of the external hemispheric dome and the member for leading air and/or carbon dioxide gas and the discharging member for the culture solution are installed on the bottom part, and in necessary occasions, the water spraying member and the water spray receiving member are installed in the outside of the cylindrical opening member and the outer circumference of the bottom part, respectively;

the cultivation apparatus with the conical shape is the cultivation apparatus comprising the external conical circumferential wall made of the clear material, the internal conical circumferential wall made of the clear material, and the bottom part connecting bottom end parts of both the circumferential wall, and the cylindrical opening member is installed on the top part of the external conical circumferential wall and the member for leading air and/or carbon dioxide gas and the discharging member for the culture solution are installed on the bottom part; and in necessary occasions, the water spraying member and the water spray receiving member are installed in the outside of the cylindrical opening member and the outer circumference of the bottom part, respectively;

or, the cultivation apparatus with the cylindrical shape is the cultivation apparatus comprising the external cylindrical circumferential wall having the upper wall made of the clear material, the internal cylindrical circumferential wall having the upper wall made of the clear material, and the bottom part connecting bottom end parts of both the circumferential wall, and the cylindrical opening member is installed on the central part of the upper wall of the external cylindrical circumferential wall and the member for leading air and/or carbon dioxide gas and the discharging member for the culture solution are installed on the bottom part, the member for leading air and/or carbon dioxide gas and the discharging member for the culture solution are installed on the bottom part, and in necessary occasions, the water spraying member and the water spray receiving member are installed in the outside of the cylindrical opening member and the outer circumference of the bottom part, respectively.

The gas discharging apparatus used for the cultivation apparatus for algae is the apparatus configured by opposite two square base boards, the bubble leading member, of which section has the square shape lacking the side or the reversed U-shape, opened downward, and the discharge nozzle, the bubble leading member is installed with inclination to the upper side face of the square base board, forms the upper wall made by extending the inclined wall of the upper face by bending almost horizontally in the upper end part, and has the side wall extending from both the side ends of the inclined wall and the upper wall, and each of the bottom end parts of both the side walls are jointed on the upper side face of the square base board, and the discharge nozzle is rotatably attached through the via hole made in the bottom part of the inclined wall, wherein in necessary occasions, at least any one of the opposite squared base boards is bent to a same direction in a front end part and/or a rear end part, and weight-adjusting means is installed in at least any one of the opposite squared base boards.

The present invention is applied to cultivation by using the cultivation apparatus in combination of the above described cultivation apparatus with the gas discharge apparatus.

For the clear material used for the cultivation apparatus, any material which is clear and excellent in light transmission performance and has weather resistance and ultraviolet resistance, can be used and is exemplified by materials such as acrylic resin, polycarbonate, polypropylene, polyethylene, polyvinyl chloride, and glass. In consideration of processibility, a synthetic resin is preferable; particularly acrylic resin having the above described characteristics is the most preferable material.

In this case, an internal material and an external material can be composed of a same clear material. Different clear materials such as the acrylic resin and polyvinyl chloride can be used for constituting the external hemispheric dome and the internal hemispheric dome, respectively. Or, Different materials may be used for layering.

Gas to be led to the cultivation apparatus must contain carbon dioxide as a component and may be that of which carbon dioxide concentration has been increased by mixing carbon dioxide with air and air and carbon dioxide may be independently led to the apparatus. In this case, gas is led to the culture solution by using a leading member or the gas discharge apparatus, and in occasion, both of these.

Most preferably, carbon dioxide is used by mixing with air. When air mixed with carbon dioxide lifts up stirring the culture solution, carbon dioxide is dispersed in the culture solution to be absorbed and air works to remove oxygen generated by cultivation from the culture solution. And, when carbon dioxide is independently led to the culture solution, a leading rate becomes low to cause inevitably a delaying tendency of a dispersion rate of carbon dioxide in the culture solution.

The cylindrical opening member has an action to disperse air injected to the culture solution, carbon dioxide gas unused, and oxygen generated to atmosphere. In the opening member opened, impurities such as waste are easy to invade. In order to prevent contamination of such matter, it is preferable to install a filter member in the opening member or the lid member is installed in the opening member to give the same action as that of the filter member.

This opening member may be formed integrally with the external hemispheric dome, the external conical circumferential wall, or the upper wall of the external cylindrical circumferential wall and may be that made by fixing that which is formed as a separate body.

The dome-shaped, conical shaped, or cylindrical shaped cultivation apparatus used as the main body of the cultivation apparatus may be integrally formed by either of the external member or the internal member, may be that of which one is integrally formed and the other is assembled with members properly divided into two or four pieces, and may be that assembled with members made by dividing both the members. Construction of the apparatus may be determined on the basis of a size and the shape of the cultivation apparatus.

In addition, for the water spray receiving member, if it is the member capable of receiving a water stream falling down on an external surface of the apparatus by spraying, the material and structure thereof are free. The material is exemplified by a metal material and a plastic material.

A structure of the water spray receiving member may be that formed as a body separated from the main body of the cultivation apparatus, that in which the receiver is constructed by extending the bottom end part of the external side member of the cultivation apparatus in a horizontal direction of the outer circumference and the front end part thereof is bent upward, and that the water spray receiver is constructed by extending the bottom end part of the internal side member of the cultivation apparatus in the horizontal direction of the outer circumference and the front end part thereof is bent upward.

It is preferable to constitute the water spray receiver with the member formed as the body separated from the main body of the cultivation apparatus.

As the member, for leading air and/or carbon dioxide gas, installed in the bottom part, a tubular member, in which a plurality of gas discharge pores are prepared, may be used and that of which bottom part has gas discharge pores in the bottom part may be used. It is not necessary to stir the culture solution mechanically by gas led from this leading member to the culture solution, because the culture solution is stirred by lifting of gas climbing up in the culture solution. Therefore, according to this method, break of algal cells by mechanical stirring or generation of the shear stress can be prevented.

Further, in accordance with lifting of gas, oxygen gas generated by photosynthesis can be efficiently and rapidly discharged from the culture solution.

Methods to supply the culture solution to the cultivation apparatus are divided in two categories. The one is the method by which a supply member (for example, a supply hole made on the bottom part) is installed in the bottom part to supply the culture solution through this supply member.

The second method is the method by which the culture solution is supplied from the cylindrical opening member of the top part. Installing various supply members and leading members in the apparatus causes complexity of the apparatus and also in case changing a species of microalgae to cultivate, contamination comes up as a problem.

Hence, the second method is more preferable one.

Both the external member and the internal member of the cultivation apparatus are composed of the clear material and thus, the artificial light source installed in the internal space of the cultivation apparatus allows cultivation in night for outdoor cultivation. In addition, in the indoor cultivation, an internal and external two artificial light sources of the cultivation apparatus allow realizing efficient continuous cultivation.

The dome-shaped cultivation apparatus occupies a small area but has a large surface area and hence, has the large light-receiving area. And, in this apparatus, stirring the culture solution is very preferably operated. On the other hand, this apparatus, in case forming with a plastic resin, it is molded readily by vacuum molding to allow preparation at the lowest cost.

From these reasons, the dome-shaped cultivation apparatus is the most preferable as the cultivation apparatus for algae.

In order to control and monitor cultivation conditions, it is preferable to install various sensors such as a temperature sensor, a liquid level sensor, a pH sensor, and a dissolved oxygen amount sensor in the cultivation apparatus. These sensors are installed through the cylindrical opening member or an external wall of the apparatus.

The gas discharge apparatus used in the present invention discharges gas such as air toward the bottom part of the cultivation apparatus in an obliquely downward direction and thus, proceeds jumping like a frog in the apparatus. By this action, the culture solution is vigorously stirred and gas which is discharged lifts in the culture solution to stir the culture solution. Particularly, in the case where algae to be cultivated is easy to form a colony, gas discharged from the gas discharge apparatus breaks the colony and algal cells are dispersed in the culture solution to increase cultivation efficiency.

The gas discharge apparatus is normally composed of the plastic resin and the weight-adjusting means is installed to adjust a weight of the apparatus.

Cultivation of algae by using such cultivation apparatus gives the following advantages: 1) no contamination of bacteria and exogenous matters, 2) easy regulation of the temperature of the culture solution, 3) no break of algal cells and no occurrence of shear stress due to capability of stirring of the liquid without mechanical stirring of the culture solution, 4) capability of increase in culture density, 5) easy cleaning of the apparatus, 6) no inhibition of cultivation by oxygen generated, and 7) a high light use efficiency. In addition, in case using the gas discharge apparatus in the culture solution, necessary gas is supplied to the culture solution by using the apparatus and thus the following advantages appear: the apparatus operates a moving motion to stir the liquid and also gas discharged stirs the liquid to make contact of gas supplied with the culture solution very good resulting in increase in cultivation efficiency.

BEST MODE FOR CARRYING OUT THE INVENTION

The cultivation apparatus used in the present invention will be described below with reference to the drawings.

Figure 1:
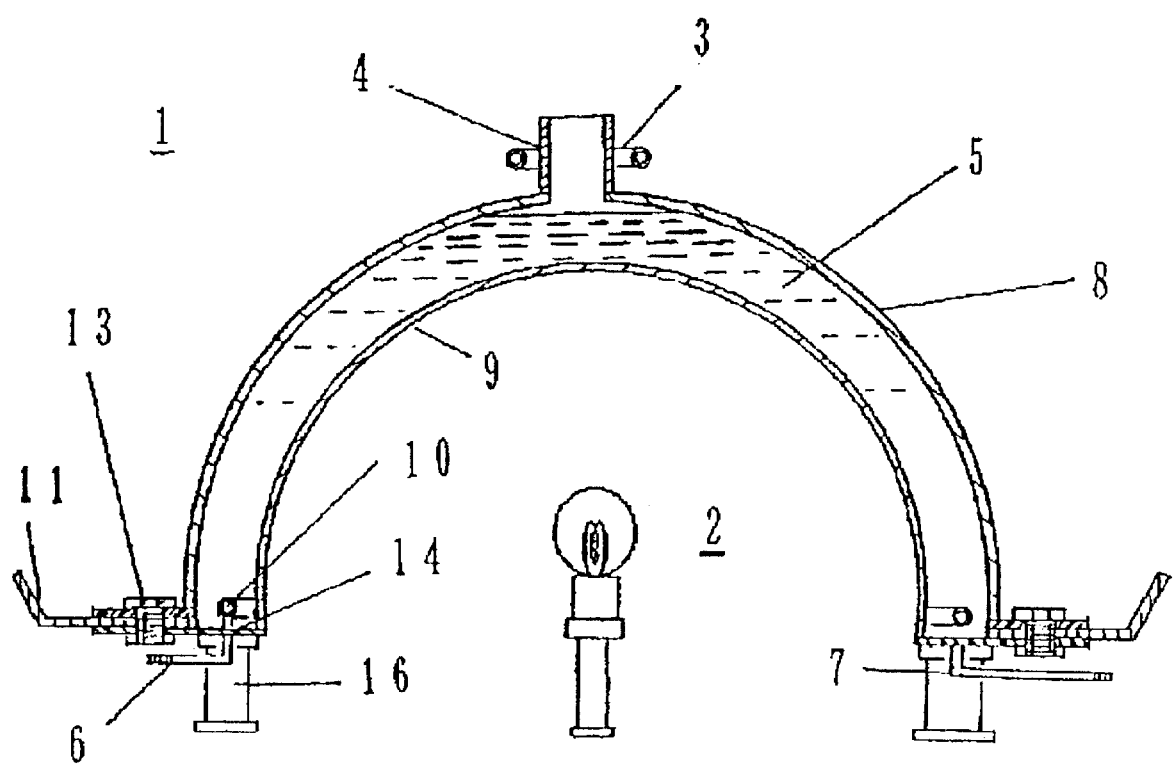
FIG. 1 is a sectional view of the dome-shaped one of the cultivation apparatus.
Figure 2:
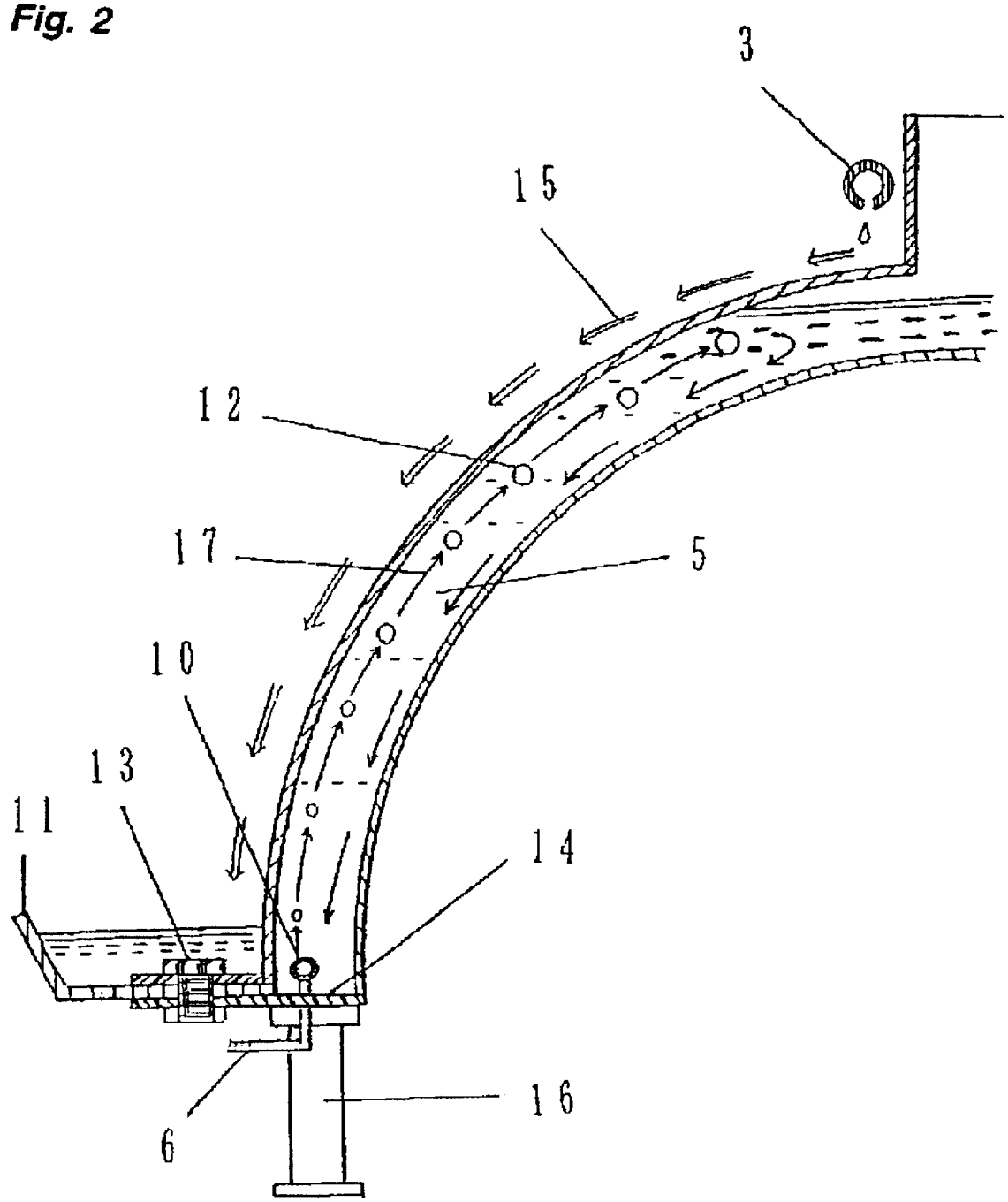
FIG. 2 is a partial schematic diagram showing a state in cultivation using the dome-shaped cultivation apparatus shown by FIG. 1.
Figure 3:
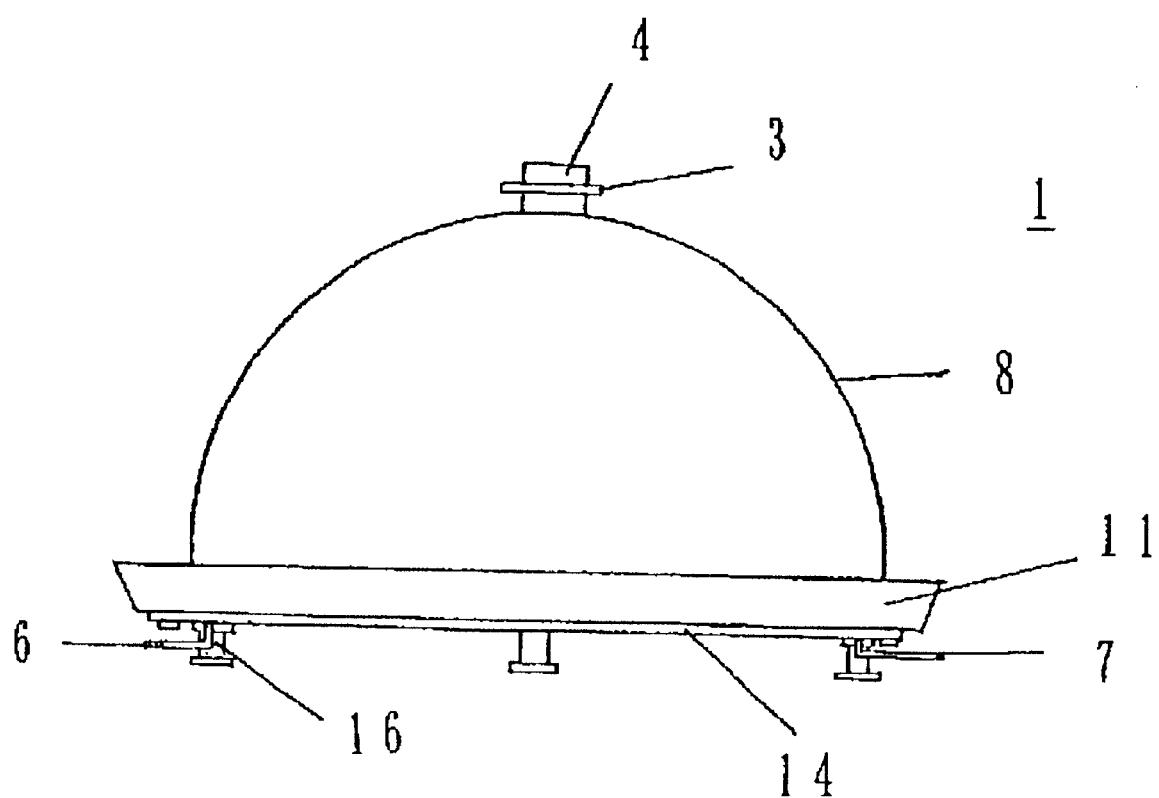
FIG. 3 is a frontal view of the dome-shaped cultivation apparatus shown by FIG. 1.

FIG. 1 to FIG. 3 show the dome-shaped one of the cultivation apparatus 1.

FIG. 3 is the frontal view of the dome-shaped cultivation apparatus 1, the cylindrical opening member 4 is installed on the top part of the external hemispheric dome 8, the water spraying member 3 to cool the dome 8 is installed in the outside of this the cylindrical opening member 4, the water spray receiving member 11 for water sprayed from the water spraying member 3 is installed in the bottom part of the dome 8, the apparatus 1 is supported by a plurality of fixing members 16. And, the gas leading member 6 and the discharging member 7 for the culture solution are installed on the bottom part 14 of the cultivation apparatus.

FIG. 1 is the sectional view of the apparatus 1. The apparatus 1 comprises the external hemispheric dome 8, the internal hemispheric dome 9, and the bottom part 14 connecting bottom end parts of both the domes. The cylindrical opening member 4 is installed as the independent body on the top part of the dome 8, the water spraying member 3 is installed in the outside of this the cylindrical opening member 4, cooling water 15 is sprayed from the water spraying member 3 to the surface of the dome 8 and falls down in a membrane form covering the surface of the dome 8 to reach the water spray receiving member 11.

Cooling water 15 regulates the temperature of the culture solution 5 (refer to FIG. 2).

The dome 8, dome 9, bottom part 14, cylindrical opening member 4, and water spray receiving member 11 are constituted by the clear material, respectively. As the clear material, the acrylic resin is used. As the material for the water spray receiving member 11, the metal material such as stainless steel can be conveniently used. Cooling water is discharged from the water spray receiving member 11 through the discharging member (not illustrated). Water discharged is reserved to use as cooling water again.

On the bottom part 14, the gas leading member 6 to supply air and/or carbon dioxide gas to the culture solution 5 and the discharging member 7 to remove the culture solution 5 from the cultivation apparatus 1 are installed. On the top face of the bottom part 14, a plurality of the gas injecting tubes 10, in which many injection holes are made on the top face of a tube, is installed to configure a part of the gas leading member 6. As gas supplied by the gas leading member 6, air mixed with carbon dioxide is most preferable; however, single use of air may be preferable.

The artificial light source 2 is installed in the internal space of the internal hemispheric dome. The artificial light source 2 allows algae to photosynthesize in case of outdoor cultivation in night. In addition, in case of indoor cultivation, algae can photosynthesize. Furthermore, in case of indoor cultivation, photosynthesis can be operated by using the artificial light source attached to the inside and outside of the cultivation apparatus. In this case, the depth or thickness of the culture solution can be increased.

FIG. 2 shows schematically the state in cultivation. Bubbles 12 of gas discharged from the gas injecting tube 10 to the culture solution 5 lifts in the culture solution 5 by buoyancy thereof along with the internal wall of the external hemispheric dome 8. Lifting motion of bubbles 12 enhances lifting of the culture solution, carbon dioxide contained in bubbles 12 is supplied to the culture solution, and oxygen generated by photosynthesis of algae is captured by bubbles. Bubbles 12 are released to atmosphere from the surface of the culture solution. A flow 17 of the culture solution lifted along with the internal wall of the external hemispheric dome 8 goes down along with the wall of the internal hemispheric dome 9.

As described above, gas such as air supplied from the bottom part or near place thereof to the culture solution supplies carbon dioxide to the culture solution and on the other hand, acts to capture oxygen generated to release to atmosphere and also acts to stir simultaneously and evenly the culture solution.

In summer, in the case where the temperature of the culture solution rises excessively to make cultivation difficult, cooling water 1b can be supplied to the surface of the external hemispheric dome 8 to regulate the temperature of the culture solution. Water used for cooling is collected through the water spray receiving member 11 to use again.

In case of the outdoor cultivation, when cultivation is operated in night, using the artificial light source 2 installed in the internal space of the internal hemispheric dome 9 allows 24-h continuous cultivation.

Algae perform photosynthesis vigorously by receiving sunlight, propagate, and produce useful substances such as a protein, polysaccharide, fatty acid, pigment, and vitamin to accumulate them. In night, such photosynthesis is not operated and thus, substance biosynthesized in day is lost in a weight of about 20% of algal cells in maximum, in comparison with the weight in day in summer, for example, through energy consumption by algae themselves. This loss is not negligible.

Therefore, in order to suppress the loss, this amount can be compensated by photosynthesis by using the artificial light source. Hence, an amount of light of the artificial light source may be for a minimum photosynthesis. However, photosynthesis above the minimum may be allowed. As the artificial light source, for example, a fluorescent light, white light, and halogen lamp are exemplified.

The indoor cultivation is operated by using the artificial light source attached to the outside and inside of the cultivation apparatus 1. As described above, using the artificial light source 2 allows 24-h efficient continuous cultivation.

For monitoring cultivation status, the temperature, liquid level, pH and dissolved oxygen (DO) amount of the culture solution must be always measured to maintain the variables in an optimal range. Therefore, sensors for these variables are preferably installed in the apparatus and preferable installation is through the cylindrical opening member 4 of the top part, or through any one of the dome 8 or dome 9 or both of them. Attaching to the dome makes the apparatus complex to require a longer time for cleaning and thus, installation through the cylindrical opening member 4 is most preferable. The dome-shaped cultivation apparatus 1, by free combination of two kinds of the hemispheric domes having different radius, a magnitude of space formed between two domes and a distance between the two domes can be changed. Consequently, a volume of the culture solution and the depth or thickness of the culture solution and can be freely determined.

Algae attach on the surface of the apparatus to which the culture solution contacts. When attachment is removed to clean, the external hemispheric dome 8 of the combined two kinds of hemispheric domes can be removed to clean each of them and both can be removed to clean in a separate place.

Assembling the hemispheric dome divided into two pieces is very convenient. By the way, the two kinds of domes may not be in the state of integral mold and molds of a plurality of separate pieces may be assembled.

Shape of the hemispheric dome may be the hemispheric dome made by cutting a spherical body in a proper position. However, in consideration of light using efficiency and light receiving status, an approximate hemispheric body is most preferable.

Not only spherical body, a deformed spherical body such as egg shaped is also of the object of the present invention.

The size of the dome usable ranges, for example, from a diameter of 50 cm to 200 cm. For the cultivation apparatus, one with a proper size may be freely chosen in accordance with species of alga to be subjected to cultivation, conditions of cultivation, and the object of cultivation.

The distance between the two kinds of domes is determined according to species of alga to be subjected to cultivation, conditions of cultivation, and the object of cultivation, however may be determined to yield the maximum photosynthesis efficiency. Normally, preferable is from 2.5 cm to 10 cm and more preferable is about 5 cm.

Next, assembling is operated for the external hemispheric dome 8 with a semidiameter of 50 cm, the internal hemispheric dome with a semidiameter of 45 cm, and the dome-shaped cultivation apparatus 1 with a dome distance of 5 cm and the cylindrical opening member 4 with the 6 cm diameter formed by molding separately from the dome 8 was installed on the top of the dome 8.

By using this cultivation apparatus, an algal species, *Spirulina platensis*, was cultivated and as a result, a cultivation density ranging from 10 g to 20 g/L (liter) and productivity ranging from 2.0 to 5.0 g/L/day were achieved. On the other hand, in case of a conventional cultivation system, the cultivation density ranged from 0.3 g to 0.5 g/L (liter) and productivity ranged from 0.1 to 0.2 g/L/day. Hence, it has been found that in comparison with the conventional cultivation method, productivity is improved to about 10 folds.

According to cultivation of *Haematococcus pulvialis* which produces astaxanthin, a red pigment, it was found that cultivation of a high density ranging from 5 g to 10 g/L as cultivation density allows production of algal cells (biomass) containing a high content of the pigment, astaxanthin, ranging from 4% to 8%. Cultivation of *Haematococcus pulvialis* to produce this red pigment is very difficult by the conventional cultivation pond system. In addition, *Nannochloropsis Oculata*, a marine microalga, could be cultivated in the density as high as a range from about 5 g to 10 g/L. The conventional method allows a limit ranging from 0.2 g to 0.4 g/L.

Figure 4:
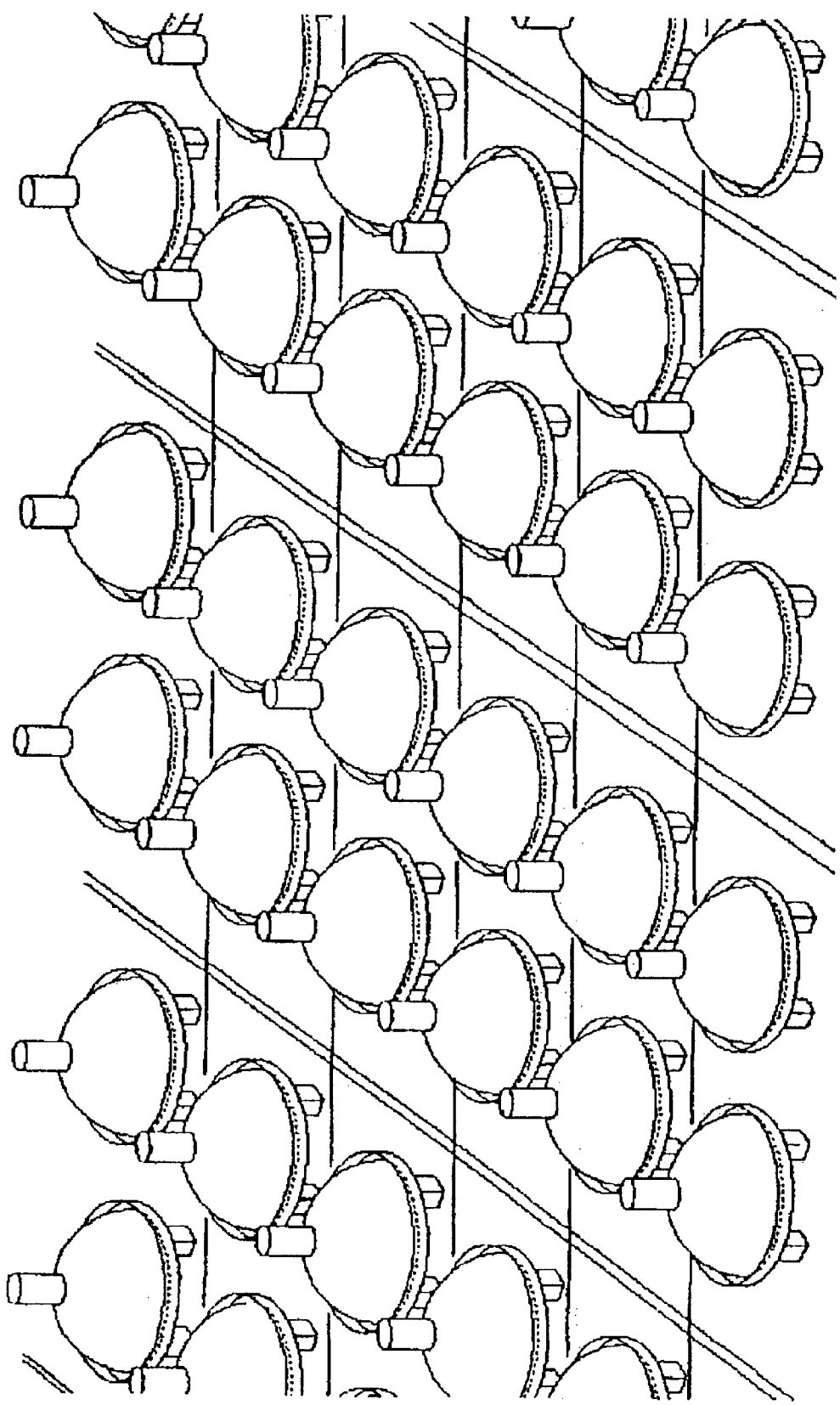
FIG. 4 is an explanatory figure showing a mass cultivation system for algae by using the dome-shaped cultivation apparatus shown by FIG. 1 to FIG. 3.

FIG. 4 shows a system capable of simultaneous and mass cultivation of algae by arranging many closed type outdoor cultivation apparatus according to the present invention. Individual apparatus composing this system can receive algae of a same species together with to cultivate them or, individual apparatus can receive algae of different species to cultivate them, and to the individual apparatus various sensors have been attached to make control of cultivation conditions possible.

Consequently, if different species of algae are cultivated in the individual apparatus, various cultivation conditions for the individual apparatus can be independently controlled to realize very effective situation.

And, even the individual apparatus are arranged in a close position in a certain degree, the light using efficiency and the light-receiving area per a unit-occupying area are large to realize very convenience, suitability for mass cultivation, and high productivity.

Figure 5:
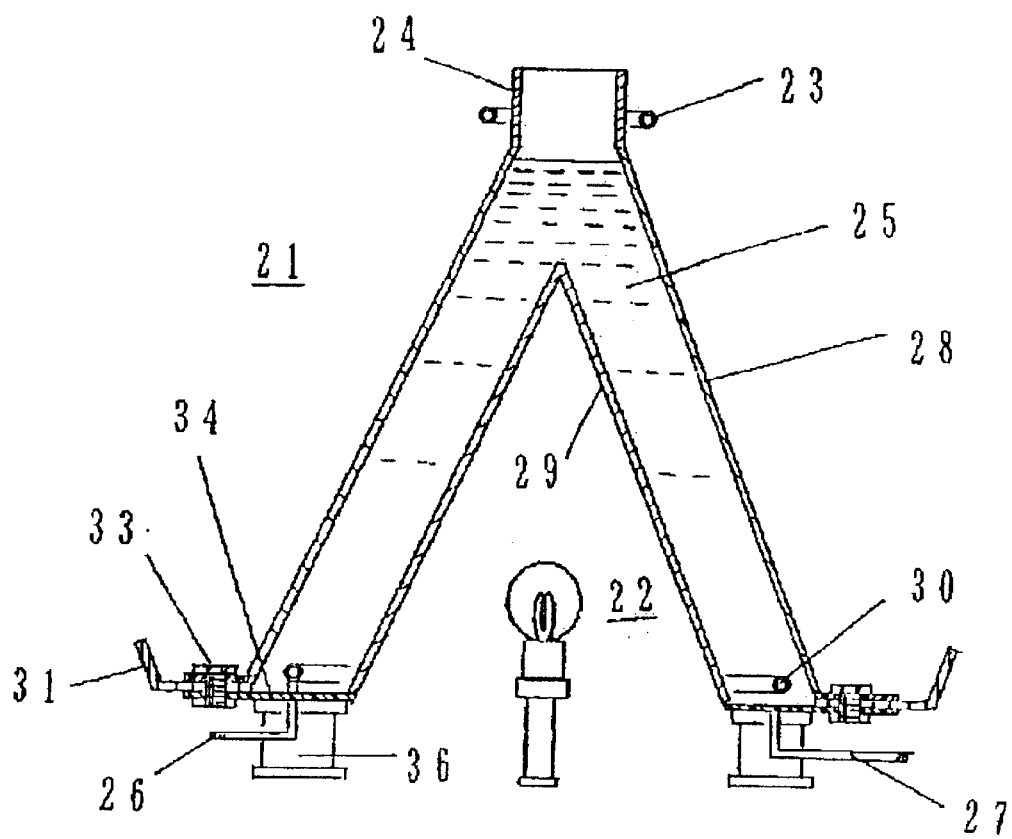
FIG. 5 is the sectional view of the conical-shaped cultivation apparatus according to the present invention.
Figure 6:
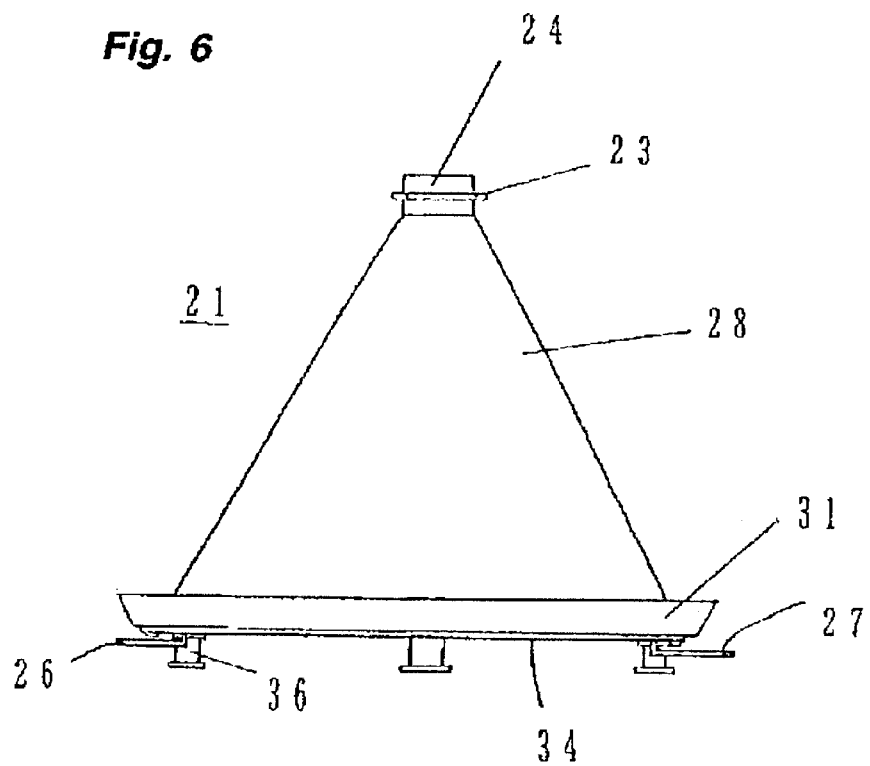
FIG. 6 is the frontal view of the conical-shaped cultivation apparatus of FIG. 5.

FIG. 5 and FIG. 6 show the conical-shaped cultivation apparatus 21.

FIG. 6 is the frontal view of the conical-shaped cultivation apparatus 21, the cylindrical opening member 24 is installed on the top part of the external conical circumferential wall 28 made from the clear material, the water spraying member 23 to cool the circumferential wall 28 is installed in the outside of the cylindrical opening member 24, the water spray receiving member 31 for cooling water sprayed from the water spraying member 23 is installed in the bottom part of the circumferential wall 28, the apparatus 21 is supported by a plurality of fixing members 36.

And, the gas leading member 26 and the discharging member 27 for the culture solution ate installed on the bottom part 34 of the cultivation apparatus 21.

FIG. 5 is the sectional view of the apparatus 21. The apparatus 21 comprises the external conical circumferential wall 28 made from the clear material, the internal conical circumferential wall 29 made from the clear material, and the bottom part 34 connecting the bottom end parts of both the circumferential walls. The cylindrical opening member 24 is installed as the independent body on the top part of the external conical circumferential wall 28, the water spraying member 23 is installed in the outside of the opening member 24, cooling water is sprayed from the water spraying member 23 to the surface of the circumferential wall 28 and fall down in a membrane form covering the surface of the circumferential wall 28 to reach the water spray receiving member 31. Cooling water regulates the temperature of the culture solution 25.

The circumferential wall 28, the circumferential wail 29, the bottom part 34, the cylindrical opening member 24, and the water spray receiving member 31 consists of the clear material such as the acrylic resin, respectively.

Cooling water is discharged from the water spray receiving member 31 through the discharging member (not illustrated).

On the bottom part 34, the gas leading member 26 to supply air and/or carbon dioxide gas to the culture solution 25 and the discharging member 27 to remove the culture solution 25 from the cultivation apparatus 21 are installed. On the top face of the bottom part 34, a plurality of the gas injecting tubes 30, in which many injection holes are made on the top face of the tube, are installed to configure a part of the gas leading member 26.

The artificial light source 22 is installed in the internal space of the circumferential wall 29 to allow continuous photosynthesize in case of outdoor cultivation in night.

Figure 7:
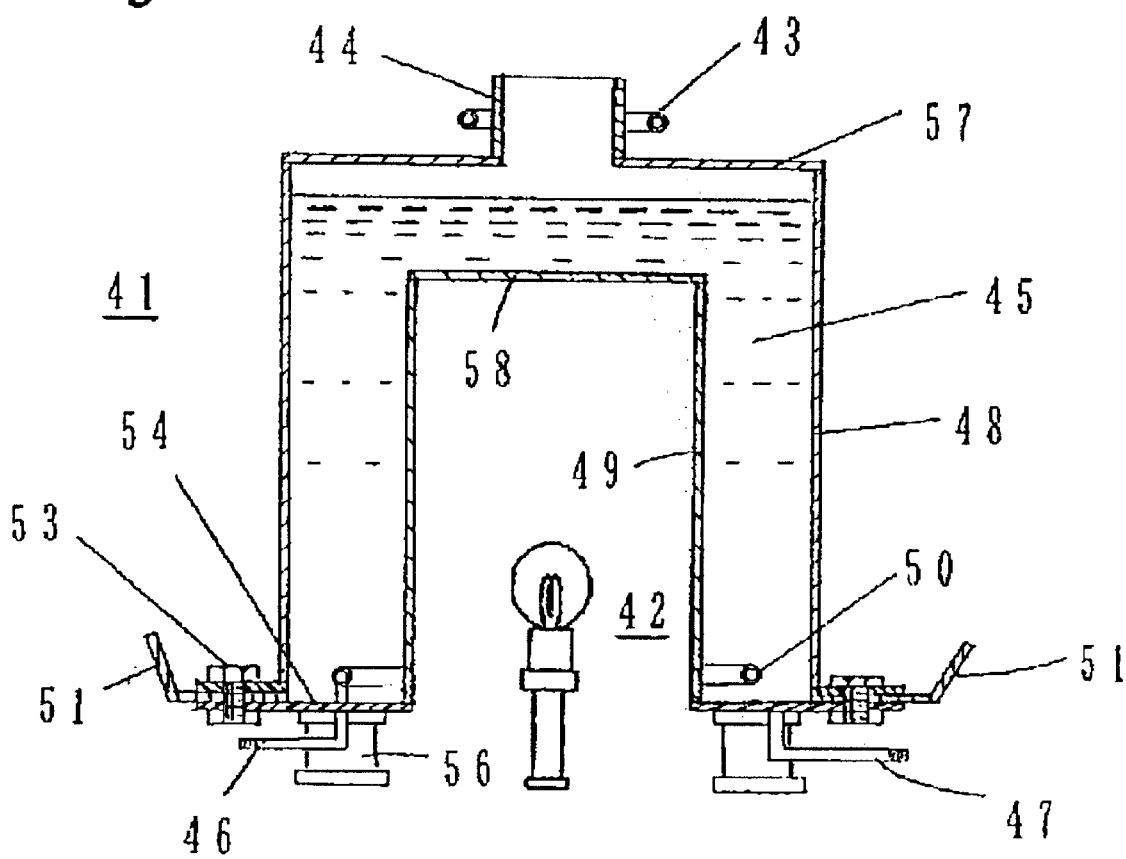
FIG. 7 is the sectional view of the cylindrical-shaped cultivation apparatus according to the present invention.
Figure 8:
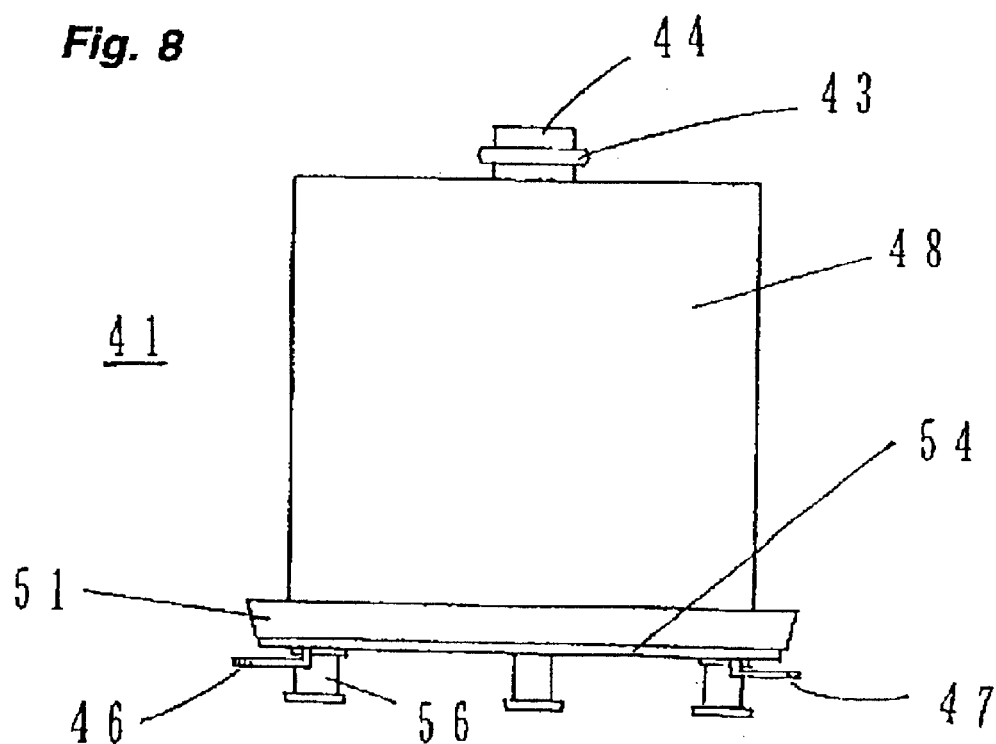
FIG. 8 is the frontal view of the cylindrical-shaped cultivation apparatus of FIG. 7.

FIG. 7 and FIG. 8 show the cylindrical-shaped cultivation apparatus 41.

FIG. 8 is the frontal view of the cylindrical-shaped cultivation apparatus 41, the cylindrical opening member 44 is installed on the central part of the upper wall of the external cylindrical circumferential wall 48 having the upper wall 57 made from the clear material, the water spraying member 43 to cool the upper wall 57 and the circumferential wall 48 is installed in the outside of the cylindrical opening member 44, the water spray receiving member 51 for cooling water sprayed from the water spraying member 43 is installed in the bottom part of the circumferential wall 48, the apparatus 41 is supported by a plurality of fixing members 56.

And, the gas leading member 46 and the discharging member 47 for the culture solution are installed on the bottom part 54 of the cultivation apparatus 41.

FIG. 7 is the sectional view of the apparatus 41. The apparatus 41 comprises the external cylindrical circumferential wall 48 having the upper wall 57, the internal cylindrical circumferential wall 49 having the upper wall 58, and the bottom part 54 connecting the bottom end parts of both the circumferential walls. The cylindrical opening member 44 is integrally installed in the central part and near place thereof of the upper wall 57, the water spraying member 43 is installed in the outside of the opening member 44, cooling water is sprayed from the water spraying member 43 to the upper wall 57 and covers the surface of the circumferential wall 48 in the membrane form to reach the water spray receiving member 51.

Cooling water regulates the temperature of the culture solution 45.

The circumferential wall 48, the circumferential wall 49, the upper wall 57, the upper wall 58, the cylindrical opening member 44, and the water spray receiving member 51 consists of the clear material such as the acrylic resin, respectively.

Cooling water is discharged from the water spray receiving member 51 through the discharging member (not illustrated). On the bottom part 54, the gas leading member 46 to supply gas to the culture solution and the discharging member 47 to remove the culture solution 45 from the cultivation apparatus 41 are installed. On the top face of the bottom part 54, a plurality of the gas injecting tubes 50, in which many injection holes are made on the top face of the tube, are installed to configure a part of the gas leading member 46.

The artificial light source 42 is installed in the internal space formed by the upper wall 58 and the circumferential wall 49 to allow photosynthesis in night.

Figure 13:
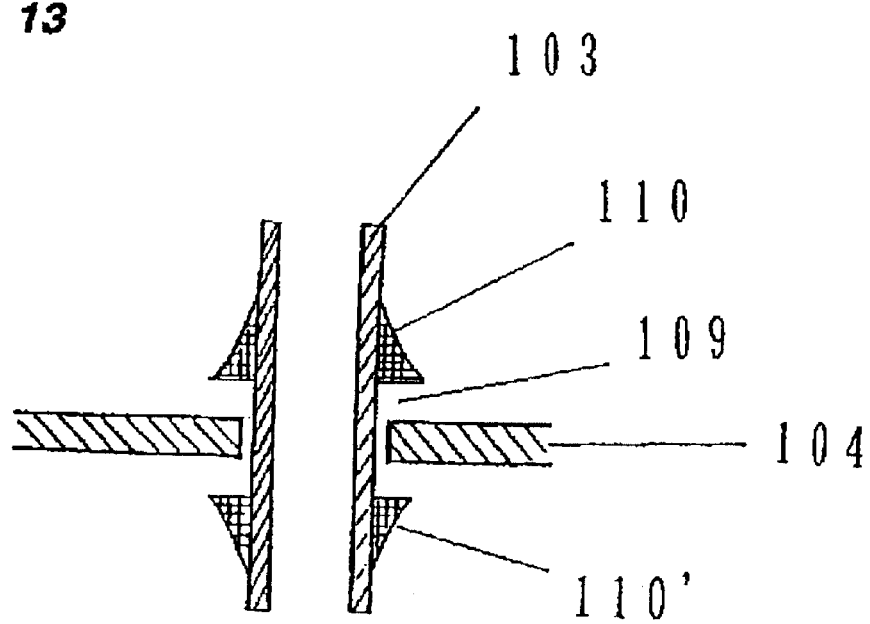
FIG. 13 is an enlarged sectional view of the discharge nozzle of the gas discharge apparatus of FIG. 9.

FIG. 9 to FIG. 12 show the perspective side view, side view, plan view, sectional view of the gas discharge apparatus 100, respectively, and FIG. 13 shows the enlarged sectional view of the discharge nozzle of the gas discharge apparatus.

The gas discharge apparatus 100 comprises the opposite two square base boards 101 and 101', the bubble leading member 102, of which section has the square shape lacking the side, opened downward, and the discharge nozzle 103, the bubble leading member 102 is installed with inclination to the upper side face 107 and 107' of the square base board, has the upper wall 105 made by extending almost horizontally the inclined wall 104 of the upper face thereof and the upper end thereof, and has the side wall 106 and 106' extending from both the side end parts of the inclined wall 104 and the upper wall 105, and the bottom end parts of both the side walls 106 and 106' are jointed on the upper side face 107 and 107' of both the square base boards 101 and 101'. Both the square base boards are fixed by the fixing members 108 and 108'.

The discharge nozzle 103 is rotatably installed through the via-hole 109 made in the bottom part of the inclined wall 104. In the nozzle 103, stoppers 110 and 110' are attached to the outer circumferential part of the nozzle 103 in opposite positions outside the via hole 109, to prevent removal from the via hole 109

Figure 11:
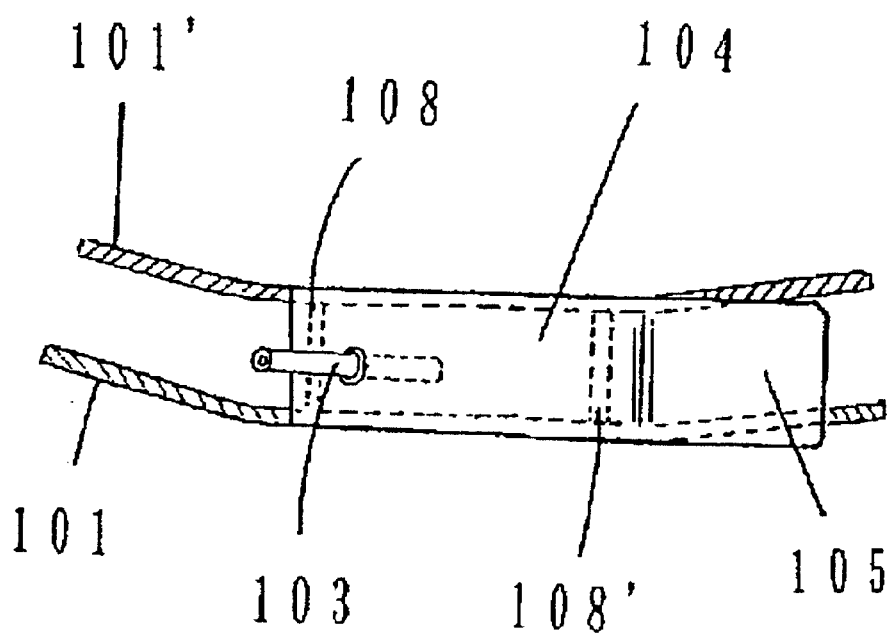
FIG. 11 is a plan view of the gas discharge apparatus of FIG. 9.
Figure 12:
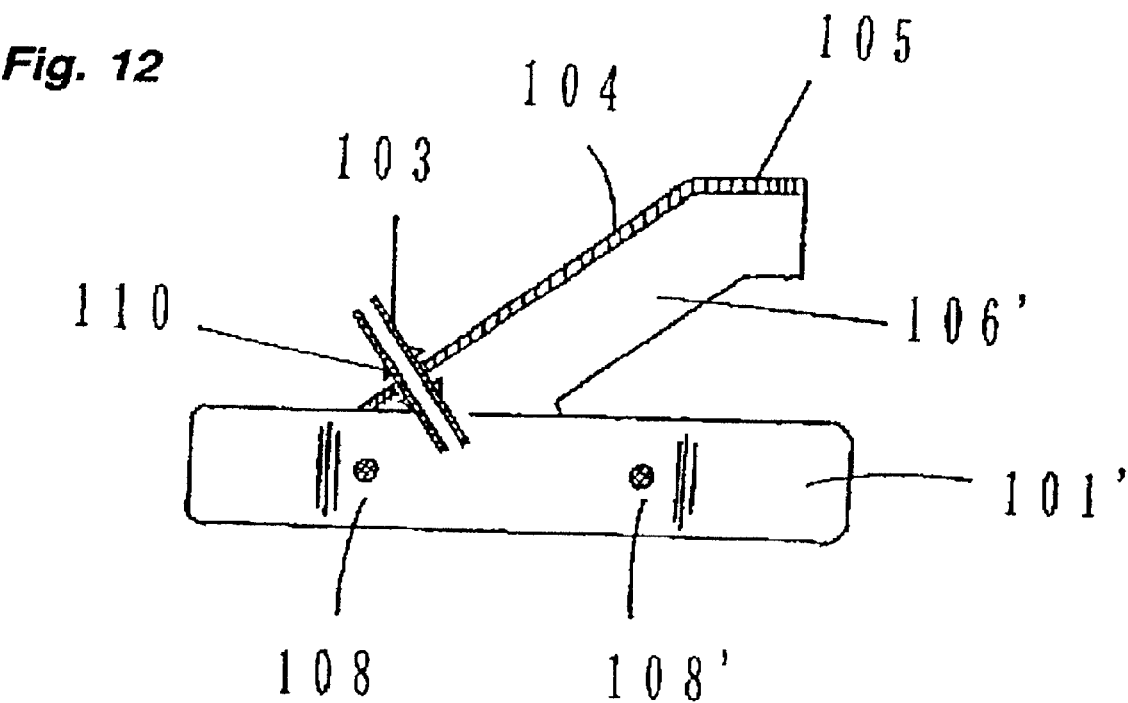
FIG. 12 is the sectional view of the gas discharge apparatus of FIG. 9.

In any one of the dome-shaped, a triangular conical-shaped, or cylindrical shaped main body of the cultivation apparatus, an internal end and an external end of the bottom part is a circumference of an concentric circle and then, shows the circle made by remove circularly the center of a circular disk. In order to move readily a columnar bottom part removed, the square base boards 101 and 101' are, as shown in FIG. 11, a frontal end part and a rear end part have been bent in a same direction.

An inclination angle of the inclined wall 104 is preferably designed to make 45° to 60° against the upper side face of the square base board.

Figure 14:
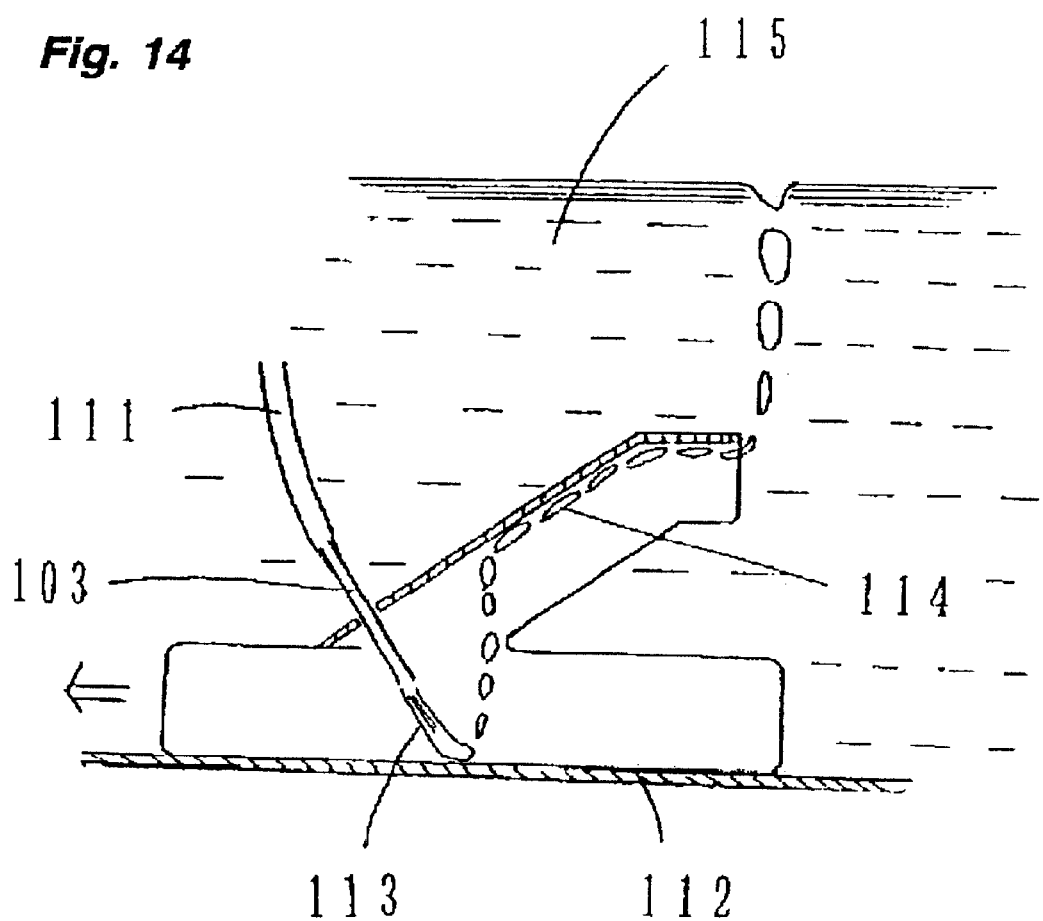
FIG. 14 is a sectional explanatory figure showing the state when the gas discharge apparatus discharges gas to the culture solution.

FIG. 14 is the explanatory figure showing the state when the gas discharge apparatus discharges gas to the culture solution.

Gas such as air or air mixed with carbon dioxide goes from a gas supply apparatus (not illustrated) separately installed from the cultivation apparatus to the discharge nozzle 103 through the gas leading tube 111 to be released from the front end thereof toward the bottom part 112 of the cultivation apparatus. Gas 113 released contacts to the bottom part 112 and then becomes bubbles 114 to lift along with the inside of a bubble leading member 102, i.e., the inclined wall 104 and the upper wall 105 and finally go out from the end part of the upper wall to the culture solution 115. Bubbles 114 gone out lift in the liquid to release to atmosphere on the surface of the culture solution. During gas is contacting to the culture solution, carbon dioxide is absorbed by the culture solution and on the other hand, air bubble or oxygen generated by photosynthesis of algae and dissolved in the culture solution is captured by gas. When lifts in the culture solution, bubbles 114 pushed simultaneously the liquid upward and hence, convection occurs.

By gas released from the front end of the discharging nozzle 103 and bubbles 114, the gas discharging apparatus itself has buoyancy and then propulsion is generated in a direction shown by an arrow. Therefore, the gas discharging apparatus 100 moves in a floating state in the direction shown by the arrow. After moved, the apparatus 100 falls on the bottom part by the weight thereof and then, floats again to go ahead; these motions are repeated and thus, this action stirs the culture solution largely. The action of the gas discharging apparatus in the culture solution likes a frog's jumping action to go ahead.

The member composing the gas discharging apparatus 100 is normally of the plastic resin. However, because the plastic resin itself is frequently light in weight and has buoyancy in the culture solution, preferable is exemplified by that molded after increasing the weight by adding a filler with a larger gravity than plastics, or that like an artificial rock molded by layering that prepared by adhering rock powder or filler powder to the square base board 101 and 101' by using such synthetic resin as epoxy-based resin, or that made by forming the bottom part of the square base board 101 and 101' by the material like the artificial rock and the upper part by plastics, or that of which total weight of the gas discharging apparatus 100 is made adjustable by making a metal weight such as lead attachable and detachable in a free position of the opposite faces of the square base board 101 and 101', The most preferable is that of which total weight is made adjustable.

Figure 15:
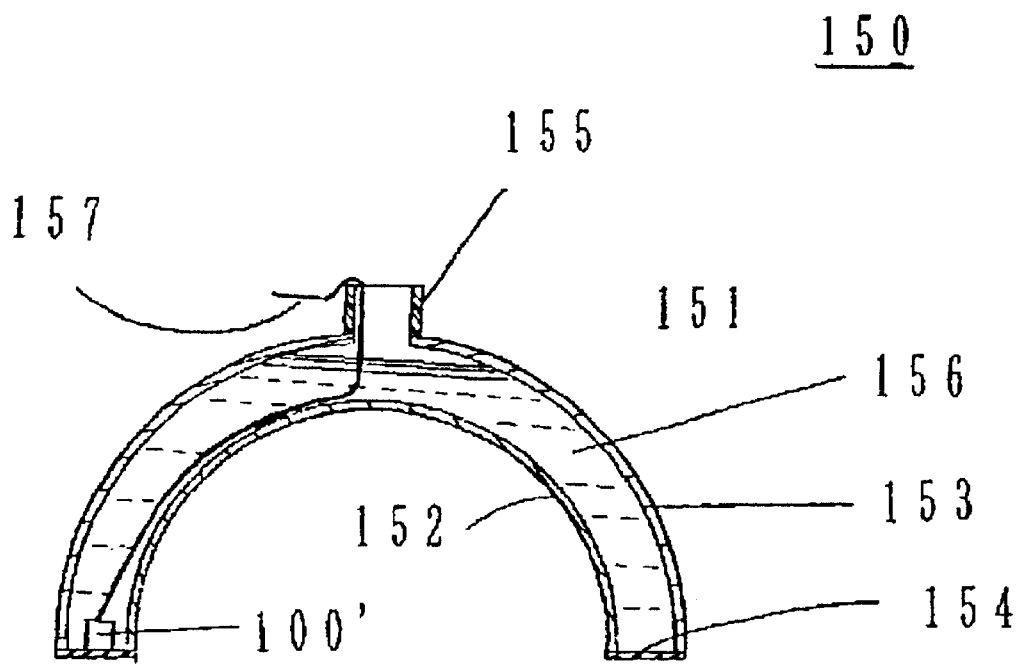
FIG. 15 is the sectional explanatory figure of the cultivation apparatus in combination of the dome-shaped cultivation apparatus itself with the gas discharge apparatus.
Figure 16:
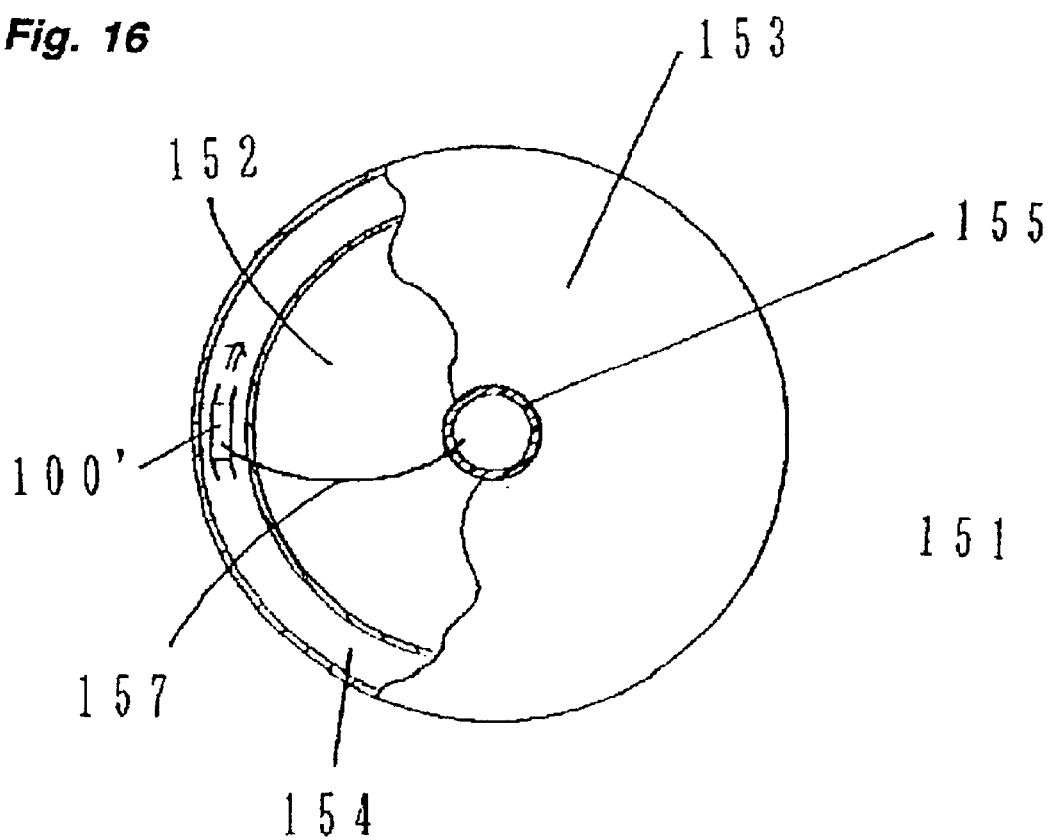
FIG. 16 is a top view, with parts broken away for the sake of clarity, of FIG. 15.

FIG. 15 is the sectional explanatory figure of the cultivation apparatus 150 in combination of the main body of the dome-shaped cultivation apparatus 151 with the gas discharge apparatus 100' and FIG. 16 is the top view thereof, with parts broken away for the sake of clarity.

Hereby, the main body of the cultivation apparatus 151 comprises the external hemispheric dome 153 and the internal hemispheric dome 152, and the bottom part 154 connecting bottom end parts of both the domes and the cylindrical opening member 155 is installed on the top part of the dome 153, and description of other members have been omitted.

The material of these members is all clear material such as the acrylic resin.

The gas discharge apparatus 100' to which the gas leading tube 157 connected is inserted from the cylindrical opening member 155 of the main body of the cultivation apparatus 151 to mount on the surface of the bottom part 154.

The gas leading tube 157 is prepared from the material such as polyurethane, silicon, or synthetic rubber and contacts to the surface of the internal hemispheric dome 152.

When gas such as air is supplied to the gas discharge apparatus 100', the apparatus 100' jumps in the culture solution to go ahead in the direction shown by the arrow. Here, by gas discharged and motion of the gas discharge apparatus, the culture solution is enough stirred.

And, the gas discharge apparatus 100' goes ahead on an annular bottom part 154 and hence, as shown in FIG. 16, the gas leading tube 157 connected rubs to clean the surface of the internal hemispheric dome 152 and simultaneously, the apparatus 100' moves circularly on the bottom part 154. Consequently, the gas leading tube 157 prevents attachment of algae on the surface of the dome 152 and also acts to clean the surface.

In addition, the gas discharge apparatus 100' moves stirring the culture solution 156 and thus, even if any algal species to form the colony exists, it is broken and dispersed again in the culture solution resulting in very efficient cultivation.

Here, twisting occurs in the gas leading tube. However, as shown in FIG. 13, the discharge nozzle is made rotatably and the discharge nozzle rotates in the via-hole to recover from twisting.

Figure 17:
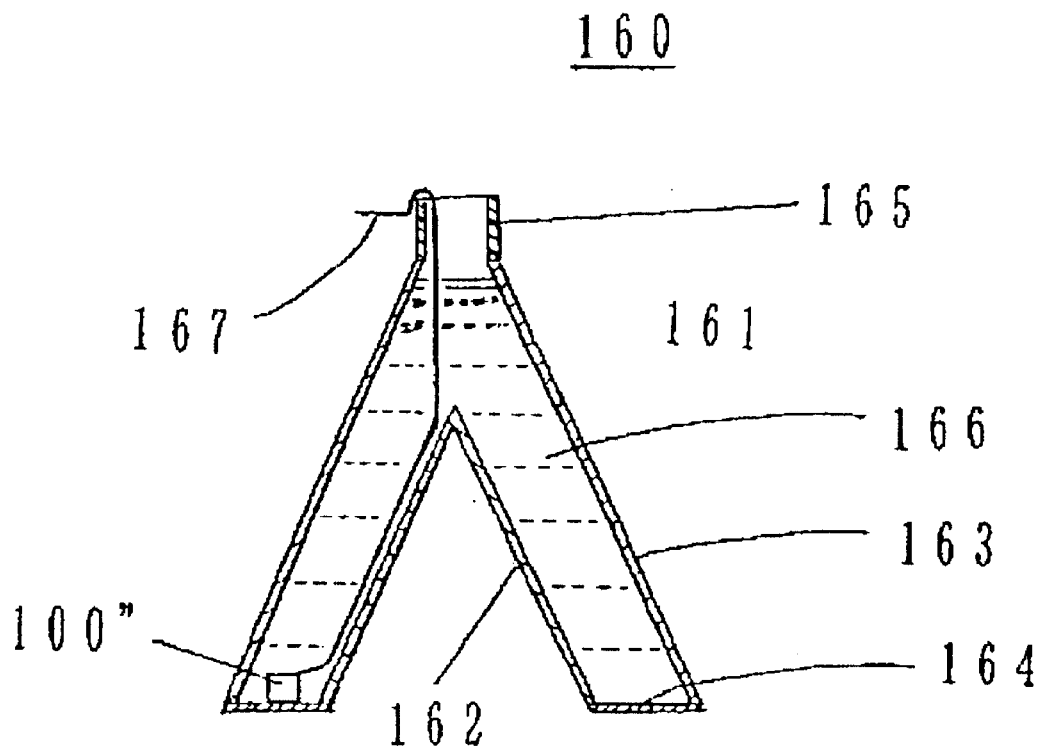
FIG. 17 is the sectional explanatory figure of the cultivation apparatus in combination of the conical-shaped cultivation apparatus itself with the gas discharge apparatus.

FIG. 17 is the sectional explanatory figure of the cultivation apparatus 160 in combination of the main body 161 of the conical-shaped cultivation apparatus with the gas discharge apparatus 100'.

Here, the main body 161 of the conical-shaped cultivation apparatus comprises the external conical circumferential wall 163 made from the clear material, the internal conical circumferential wall 162 made from the clear material, and the bottom part 164 connecting the bottom end parts of both the circumferential walls and the cylindrical opening member 165 made from the clear material is installed on the bottom part of the circumferential wall 163. Hereby, description of other members has been omitted.

The gas discharge apparatus 100' to which the gas leading tube 167 connected is inserted from the cylindrical opening member 165 to mount on the bottom part 164.

When gas such as air is supplied to the gas discharge apparatus 100', the apparatus 100' jumps in the culture solution to repeat propulsion motion. This motion has been explained for the cultivation apparatus in FIG. 15 and FIG. 16.

Figure 18:
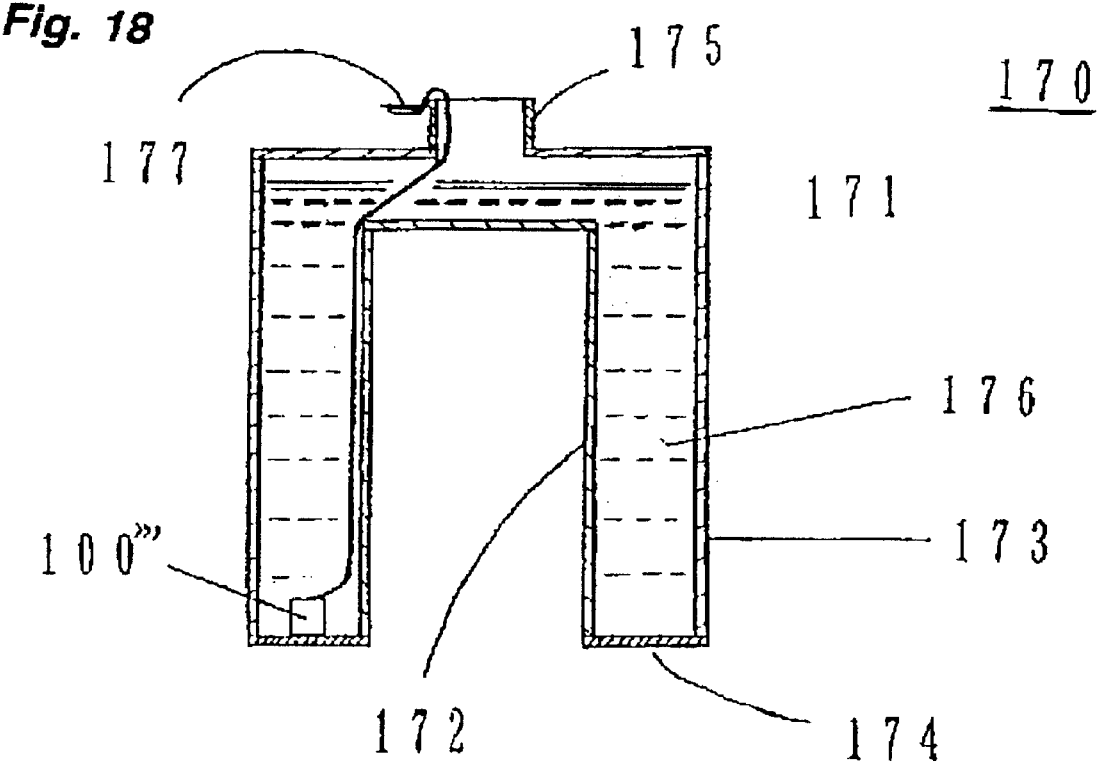
FIG. 18 is the sectional explanatory figure of the cultivation apparatus in combination of the cylindrical-shaped cultivation apparatus itself with the gas discharge apparatus.

FIG. 18 is the sectional explanatory figure of the cultivation apparatus 170 in combination of the main body 171 of the cylindrical-shaped cultivation apparatus with the gas discharge apparatus 100'''.

Hereby, the main body 171 of the cultivation apparatus comprises the external cylindrical circumferential wall 173 having the upper wall 57 made from the clear material, the internal cylindrical circumferential wall 49 having the upper wall 172 made from the clear material, and the bottom part 174 connecting the bottom end parts of both the circumferential walls and the cylindrical opening member 175 made from the clear material is installed in the central part of the upper wall of the external cylindrical circumferential wall 173. Hereby, description of other members has been omitted.

The gas discharge apparatus 100' to which the gas leading tube 177 connected is inserted from the cylindrical opening member 175 to mount on the bottom part 174.

When gas such as air is supplied to the gas discharge apparatus 100''', the apparatus 100''' jumps in the culture solution to repeat propulsion motion. This motion has been explained for the cultivation apparatus in FIG. 15 and FIG. 16.

Figure 19:
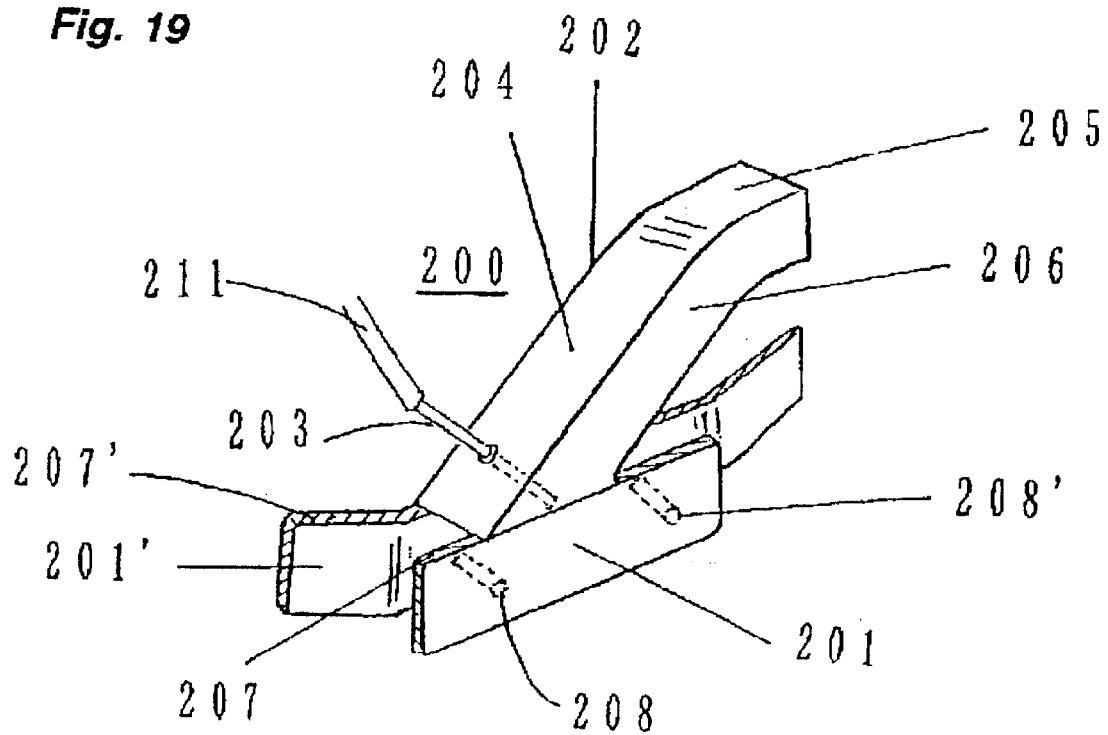
FIG. 19 is the perspective side view of another example of the gas discharge apparatus of the present invention.

FIG. 19 is the perspective side view showing another example of the gas discharge apparatus used in the present invention.

Figure 9:
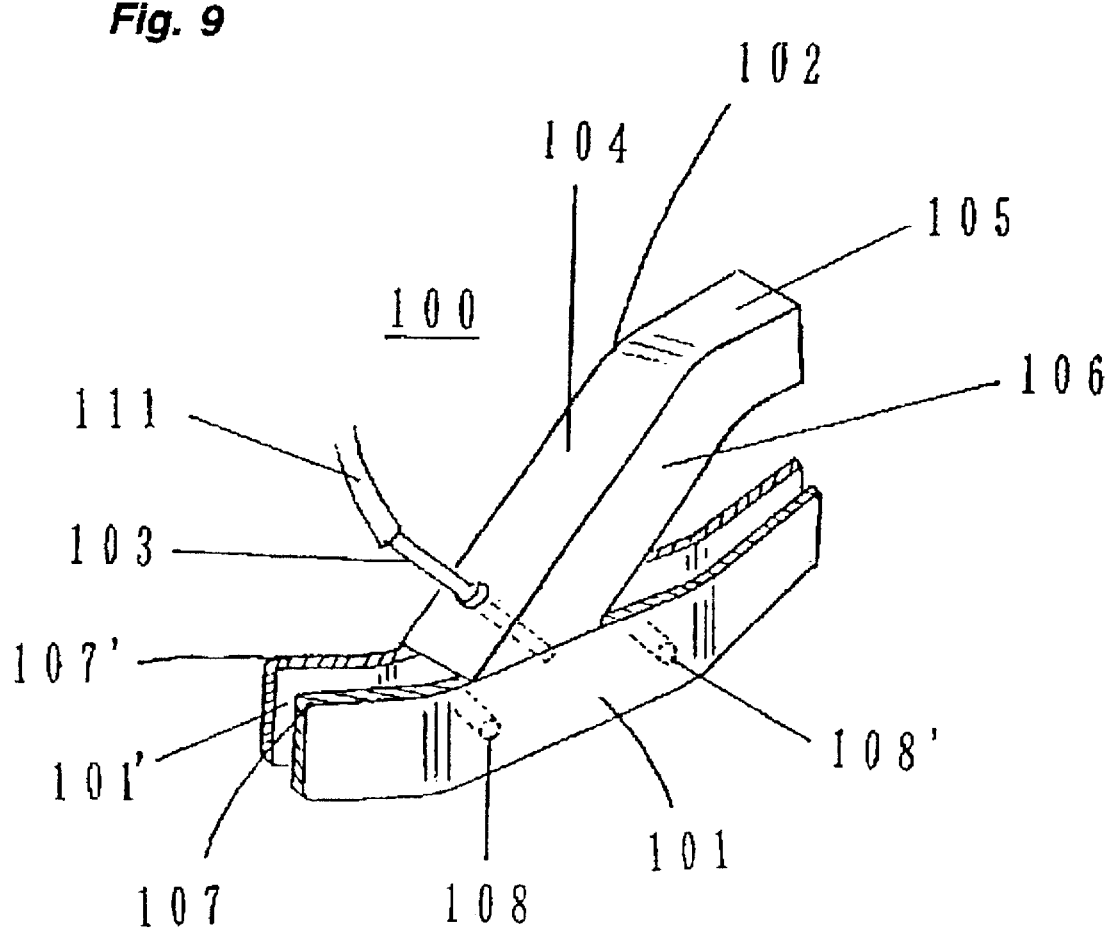
FIG. 9 is a perspective side view of the gas discharge apparatus.
Figure 10:
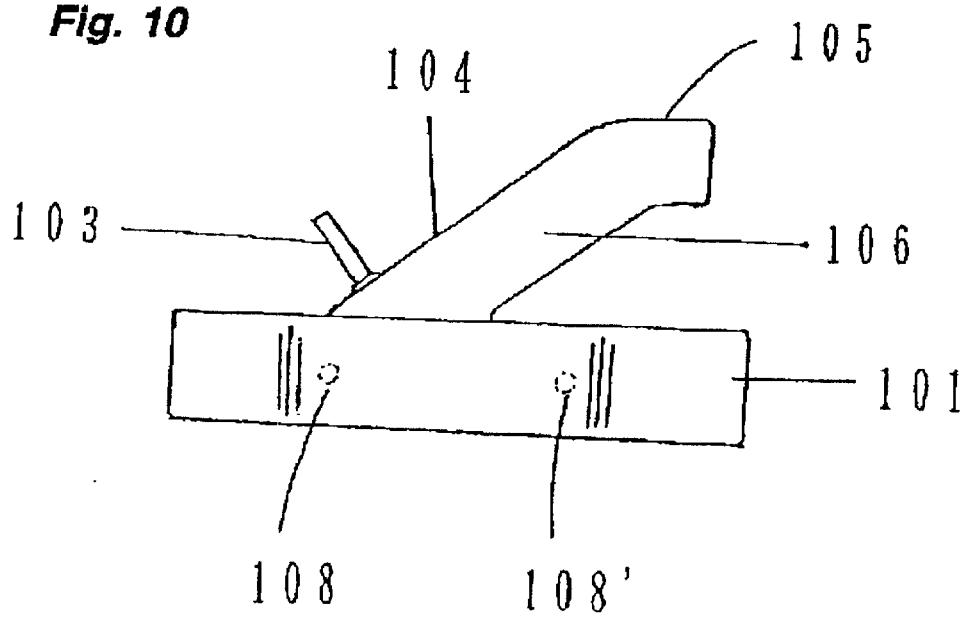
FIG. 10 is a side view of the gas discharge apparatus of FIG. 9.

This gas discharge apparatus 200 has a structure different from the gas discharge apparatus 100 of FIG. 9 in the point, that among opposite square base boards 201 and 201', the one square base boards 201 has a shorter length than that of the other square base boards 201' and the frontal end part and the rear end part have been bent in the same direction; however, other points are same. And, a reference numeral 202 is the bubble leading member, a reference numeral 203 is the discharging nozzle, a reference numeral 211 is the gas leading tube, reference numerals 201 and 201' are the square base boards, a reference numeral 204 is the inclining wall, a reference numeral 205 is the upper wall, a reference numeral 206 is the side wall, reference numerals 207 and 207' are upper side walls, and reference numerals 208 and 208' are the fixed members, respectively.

On the other hand, the weight (not illustrated), which is weight-adjusting means, is attached attachably and detachably on the square base board 201 and 201'.

Figure 20:
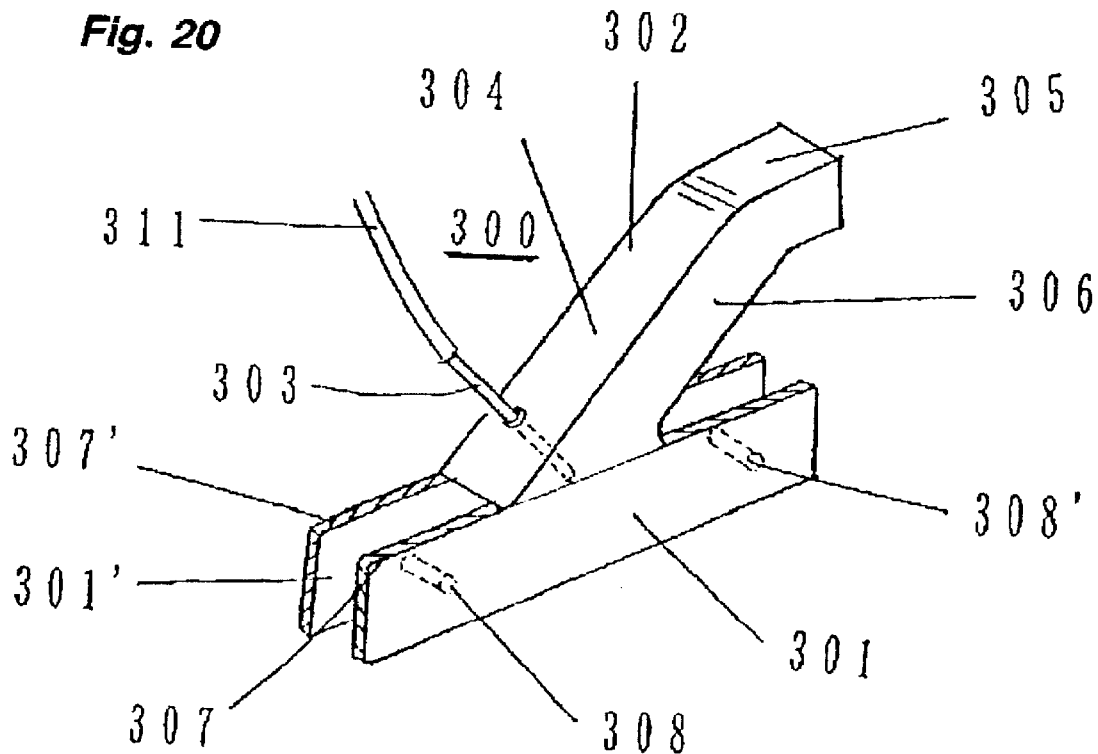
FIG. 20 is the perspective side view of another example of the gas discharge apparatus of the present invention.

FIG. 20 is the perspective side view of other example of the gas discharge apparatus used in the present invention.

This gas discharge apparatus 300 has the structure different from the gas discharge apparatus 100 of FIG. 9 in the point, that both the opposite square base boards 301 and 301' have not been bent in the frontal end part and the rear end part; however, other points are same. And, a reference numeral 302 is the bubble leading member, a reference numeral 303 is the discharging nozzle, a reference numeral 311 is the gas leading tube, reference numerals 301 and 301' are the square base boards, a reference numeral 304 is the inclining wall, a reference numeral 305 is the upper wall, a reference numeral 306 is the side wall, reference numerals 307 and 307' are upper side walls of the square base boards, and reference numerals 308 and 308' are the fixed members, respectively.

On the other hand, the weight (not illustrated), which is weight-adjusting means, is attached attachably and detachably to the square base board 301 and 301'.

Figure 21:
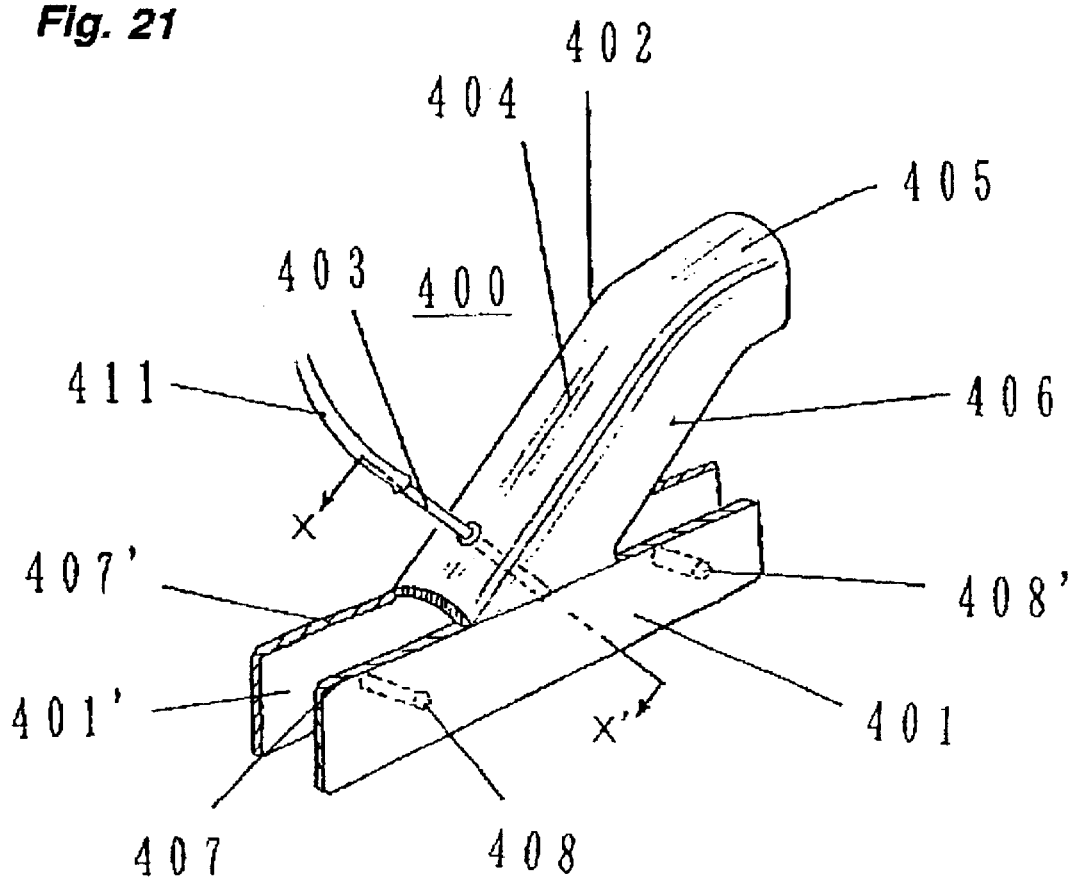
FIG. 21 is the perspective side view of further example of the gas discharge apparatus of the present invention.

FIG. 21 is the perspective side view of further example of the gas discharge apparatus used in the invention of the present application.

Figure 22:
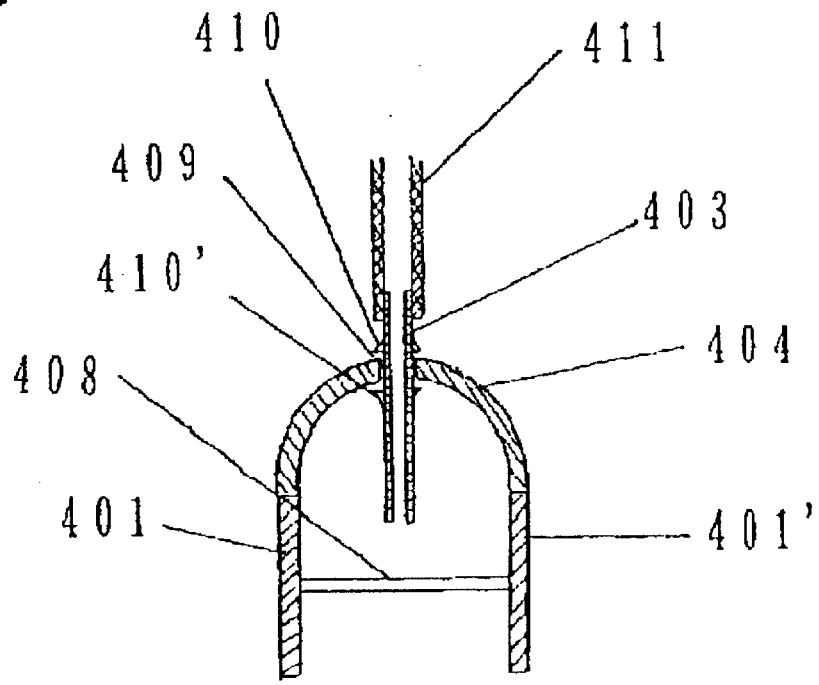
FIG. 22 is an X–X' sectional view in FIG. 21.

FIG. 22 shows the X–X' sectional view of the gas discharge apparatus in FIG. 21.

This gas discharge apparatus 400 comprises the opposite square base boards 401 and 401' and the bubble leading member 402 having a shape of the reversed U-shape in section opened downward and bent shape in an external shape, and the discharge nozzle 403 to which the gas leading tube 411 is connected, wherein the gas leading 402 is installed inclining to the upper side faces 407 and 407' of the square base board part and has the reverse U-shaped structure in section, in which the upper end part of a semicircular inclining wall 404 in the upper face thereof forms the upper wall 405 extending by bending almost horizontally keeping the semicircular shape, and has both the side walls (comprising wall 406 and other wall (not illustrated)) extending from the semicircular side end part and the bottom end parts of the above described both the side walls are jointed on the upper side faces 407 and 407' of the square base board. The discharge nozzle 403 is rotatably attached through the via hole 409 made on the semicircular top part located beneath the inclined wall 404 of the bubble leading member 402 having a section of the reverse U-shape, and in order to prevent removal from the via hole 409, two stoppers 410 and 410' are installed outside the via hole 409 in the external circumferential part of the discharging nozzle 403 in the opposite position.

The end part formed by the upper wall 405 and both the side walls is opened and the square base boards 401 and 401' are fixed by the fixing members 408 and 408'.

In this example, the two square base boards have not been bent in the frontal end part and the rear end part; however, the frontal end part and the rear end part of the two square base boards may be bent in the same direction and those having the structure in which the one of the square base boards bent in the frontal end part and/or the rear end part may be used as well.

To the square base boards 401' and 401', the weight (not illustrated), which is weight adjusting means, is attached attachably and detachably.

As the cultivation apparatus among the cultivation apparatus, for algae, developed by the present inventors, by using the dome type cultivation apparatus for algae (hereafter, cultivation apparatus A) as a representative example, the present invention will be described below.

The first of the present invention is the method for manufacturing algal cells (biomass) by the method for cultivation of algae in the high density, employing the cultivation apparatus A.

According to the present invention, cultivation of algal cells (biomass) in the high density includes various types and can be unspecified and varies according to the structure of the cultivation apparatus, the volume of the cultivation apparatus, species of the alga used, an initial density of algal cells, the kind of the culture solution, a composition of the culture solution, a pH of the culture solution, the temperature of cultivation, the light quantity irradiated on a cultivation container, irradiation time, duration of cultivation, the composition in aeration (air and a mixture gas of air and carbon dioxide), an aeration rate, presence or absence of an additive such as a plant growth hormone regulating growth of a plant, presence or absence of a scavenger for removal of an activated oxygen, and the like. Normally, the cultivation is that conducted in the range of cultivation density from 1 g to 10 g/L (liter), preferably from 3 g to 6 g/L, and more preferably from 5 g to 6 g/L.

According to the present invention, preferably usable algal species, which can produce the highly unsaturated fatty acid, the photosynthetic pigment, and/or the polysaccharide, and be cultivated in the high density, are exemplified by those described in Chihara Mitsuo "Biology of algal diversity" (1997). Specifically, Division Cyanophyta (Myxophyta) Class Cyanophyceae (Nostocophyceae), Division Prochlorophyta Class Prochlorophyceae, Division Glaucophyta (Glaucocystaphyta), Class Glaucophyceae (Glaucocystophyceae), Division Rhodophyta, Class Rhodophyceae (Bangiophyceae), Division Cryptophyta, Division Cryptophyceae, Division Dinophyta (Pyrrhophyta) Class Dinophyceae, Division Heterokontophyta, Chromophyta Class Chrysophyceae, Class Xanthophyceae (Tribophyceae), Class Eustigmatophyceae, Class Raphidophyceae, Class Bacillariophyceae (Diatomophyceae), Class Phaeophyceae (Fucophyceae), Division Haptophyta (Prymnesiophyta), Class Haptophyceae (Prymnesiophyceae), Division Euglenophyta Class Euglenophyceae, Division Chlorarachniophyta Class Chlorarachniophyceae, Division Chlorophyta Class Chlorophyceae (sensu lato), Class Prasinophyceae, Class Pedinophyceae, Division Chlorophyta, Class Prasinophyceae, Class Pedinophyceae (sensu stricto), Class Chlorophyceae, Class Trebouxiophyceae, and Class Ulvophyceae.

More specifically, algal taxa belonging to the Cyanophyceae are those being Prokaryotae, which have ability of oxygen evolution type photosynthesis and are classified into the following orders and families.

Chroococcales includes Microcystaceae, Chroococcaceae, Entophysalidaceae, Chamaesiphoniaceae, Dermocarpellaceae, Xenococcaceae, and Hydrococcaceae, Oscillatoriales includes Borziaceae, Pseudanabaenaceae, Schizotrichaceae, Phormidiaceae, Oscillatoriaceae, and Homoeotrichaceae, Nostocales includes Scytonemataceae, Microchaetaceae, Rivulariaceae, and Nostocaceae, and Stigonematales includes Chlorogloeopsaceae, Capsosiraceae, Stigonemataceae, Fischerellaceae Borzinemataceae, Nostochopsaceae, and Mastigocladaceae.

*Algal taxa* belonging to the Prochlorophyceae are those being Prokaryotae, which have ability of oxygen evolution type photosynthesis and are classified into the following orders and families. Prochlorales includes Prochloraceae and Prochlorotrichaceae.

*Alga taxa* belonging to the Glaucophyceae are those which have unicellular or colonial structure and ability of photosynthesis by cyanophyte symbiont, replacing to a chloroplast, living in algal cells, and are classified into the following orders and families. Cyanophorales includes Cyanophoraceae, Gloeochaetales includes Glaucosphaeraceae and Gloeochataceae, and Glaucocystales includes Glaucocystaceae.

Rhodophyceae have 600 genera and 5000 species and classified into the following subclasses, orders, and families. Rhodophyceae is distributed widely to fresh water and brackish waters and includes Bangiophycidae and Nemaliophycidae.

Bangiophycidae includes Porphyridiales, Porphyridiaceae, Cyanidiaceae, Goniotrichiaceae, and Erythropeltidales.

Of the Nemaliophycidae, Acrochaetiales includes Acrochaetiaceae, Palmariales includes Rhodophysemataceae and Palmariaceae, and Nemaliales includes Nemaliaceae.

*Algal taxa* belonging to the Cryptophyceae are unicellular flagellates, distributed in any freshwater, brackish and marine waters, and classified into the following orders and families. Cryptomonadales includes Cryptomonadaceae, Cryptochrysidaceae, Goniomonadaceae, Katablepharidaceae, and Hemiselmidaceae.

*Algal taxa* belonging to the Dinophyceae are distributed in any freshwater, brackish and marine waters, and classified into the following orders and families. Noctilucales, Prorocentrales, Dinophysiales, Gymnodiniales, Peridiniales, Gonyaulacales, Blastdiniales, and Phytodiniales.

*Algal taxa* belonging to the Chrysophyceae of Heterokontophyta are classified into the following orders and families. Ochromonadales includes Ochhromonadaceae, Dynobryaceae, Chlomulinaceae, Chsamoebaceae, Rhizochrysidaceae, and Lepochromulinaceae, Phaeothamiales includes Phaeothamniaceae, Thallochrysidales includes Thallochrysidaceae, Hydrurales includes Hydrudaceae, and Synurales includes Synuraceae.

Xanthophyceae distributed in freshwater areas is an *algal taxon* belonging to Heterokontophyta and classified into the following orders. Chloramoebales, Rhizochloridales, Mischococcales, Tribonematales, and Vaucheriales.

*Algal taxa* belonging to the Eustigmatophyceae are unicellular, distributed mainly to freshwater areas and a few are found from marine waters, and classified into the following orders and families. Eustigmatales includes Class Raphidophyceae, Class Bacillariophyceae (Diatomophyceae), and Class Phaeophyceae (Fucophyceae).

Among the above described *algal taxa*, when algae are cultivated in the high density and the high light using efficiency by employing the cultivation apparatus of the present invention, particularly preferably used are Chlorella, Spirulina, and Dunaliella.

Algae for cultivation according to the present invention can be those of the above described various *taxa*, algae are the most preferable on the basis of size and easy cultivation, and algal species of a fairly large size can be cultivated.

The above described Spirulina belongs to the Family Oscillatoriaceae of the Order Nostocales of the Class Cyanophyceae and is filamentous and planktonic. More specifically, *Spirulina platensis, Spirulina maxima, Spirulina geitleri, Spirulina siamise, Spirulina major, Spirulina subsalsa, Spirulina princeps, Spirulina laxissimza, Spirulina curta*, and *Spirulina sprulinoides* are exemplified and easily available *Spirulina platensis, Spirulina maxima, Spirulina geitleri*, and *Spirulina siamise* are preferable.

The method according to the present invention for high density cultivation of the above described algal species by using the cultivation apparatus A will be described below.

The method for manufacture of algal cells (biomass) by high density cultivation according to the present invention can be unspecified and varies according to the structure of the cultivation apparatus, the volume of the cultivation apparatus, species of the alga used, the initial density of algal cells, the kind of the culture solution, the composition of the culture solution, the pH of the culture solution, the temperature of cultivation, the light quantity irradiated on a cultivation container, irradiation time, duration of cultivation, the composition in aeration (of air and the mixture gas of air and carbon dioxide), the aeration rate, presence or absence of the additive such as the plant growth hormone regulating growth of the plant, presence or absence of the scavenger for removal of an activated oxygen, and the like; however, normally, the cultivation is that conducted in the range of cultivation density from 1 g to 10 g/L (liter), preferably from 3 g to 10 g/L, and more preferably from 5 g to 10 g/L.

According to the cultivation method (open pond system) conventionally operated in a practical scale, the initial cultivation density of algal cells ranges from 0.05 to 0.1 g/L (liter) and a final (harvest) cultivation density ranges from 0.5 to 0.8 g/L. The cultivation density above 1.0 g/L is called the high density cultivation.

In the present specification, the high density cultivation is defined as the range from 1.0 to 10.0 g/L (liter). When a light path in a biodome is reduced, 10 g/L cultivation becomes possible.

The above described cultivation apparatus can be chosen from various cultivation apparatus described in the specification submitted for application (PCT/JP99/1585) by the present inventors. Preferably, it is the dome-shaped structure.

The volume of the cultivation apparatus is not specially restricted; however, for maintenance and management, normally 60 to 150 liter (L) and preferably 80 to 120 liter (L).

The initial cultivation density of algal cells for algal species used varies according to the kind of the culture solution, the composition of the culture solution, the pH of the culture solution, the temperature of cultivation, the light quantity irradiated on a cultivation container, irradiation time, the composition in aeration (air and a proportion of the mixture gas of air and carbon dioxide), the aeration rate, and is not restricted; however, preferably ranges normally from 0.03 to 0.5 g/L.

Culture solution varies according to algal species usable are fresh water, seawater, and that prepared by diluting seawater, brackish water, and media a publicly known as an artificial medium or prepared by following a publicly known method.

The pH of the culture solution varies according to the kind of the culture solution and species of alga, which are used, and is not restricted; however, preferably ranges normally from pH 5.5 to pH 9.0, preferably from pH 7.0 to pH 8.0. Specifically, in case of Spirulina species, 8 to 11, preferably 8.5 to near 10, in Haematococcus species pH 6.0 to 8.5, preferably 6.5 to near 7.5, in *Nannnochloropsis oculata* pH 6.5 to 8.5, preferably 7.0 to near 8.0.

The temperature of the medium varies according to species of alga and is not restricted; however, preferably ranges normally from 15° C. to 35° C. as a proper temperature. For example, in case of Spirulina species, preferable temperature ranges from 25° C. to 35° C., in Haematococcus species preferable temperature ranges from 20° C. to 28° C., in *Nannnochloropsis oculata* preferable temperature ranges from 25° C. to 30° C.

Solar radiation quantity varies according to species of alga used and is not restricted; however, for example, in case cultivating Spirulina species in a 120 liter of the cultivation volume, about 18 MJ is preferable.

Duration of solar radiation varies according to species of alga cultivated and the temperature of culture is not restricted; however, a range from 10 h to 14 h is preferable.

Aeration rate varies according to the volume of the cultivation container, air, and the mixture gas of air and carbon dioxide (carbon dioxide concentration is 2.0%) and is not restricted however, for example, in case of 120 liter of the cultivation volume, ranges from 20 liter/min to 30 liter/min, and preferably ranges from 25 liter/min to 30 liter/min.

A cultivation period is about 10 days and preferably shorter than 10 days.

Algal cells (biomass) yielded can be separated by a common method for example through filtering, centrifuging, washing, and drying algal cells contained in the culture solution.

The second of the present invention if the method for manufacturing algal cells containing a high content of photosynthetic pigments by the high density cultivation method using the cultivation apparatus A.

According to the present invention, the high density cultivation of algal cells containing photosynthetic pigments can be unspecified and varies according to the structure of the cultivation apparatus, the volume of the cultivation apparatus, species of the alga used, the initial density of algal cells, the kind of the culture solution, the composition of the culture solution, the pH of the culture solution, the temperature of cultivation, the light quantity irradiated on the cultivation container, irradiation time, duration of cultivation, the composition in aeration (of air and the mixture gas of air and carbon dioxide), the aeration rate, a method for cyst formation, presence or absence of the additive such as the plant growth hormone regulating growth of the plant, presence or absence of the scavenger for removal of an activated oxygen, and the like; however, normally, the cultivation is that conducted, in the range of cultivation density from 1 g to 10 g/L, preferably from 3 g to 10 g/L, and more preferably from 5 g to 10 g/L, and content of photosynthetic pigments yielded per dry weight algal cells ranges 0.8% to 9%, preferably 4% to 9%, more preferably 7% to 9%.

The above described photosynthetic pigments are carotenoid pigments exemplified by astaxanthin, antheraxanthin, alloxanthin, violaxanthin, echinenon, oscillaxanthin, carotene, canthaxanthin, cryptoxanthin, chloroxanthin, siphonaxanthin, siphonein, zeaxanthin, diadinoxanthin, diatoxanthin, dinoxanthin, neoxanthin, neofucoxanthin, fucoxanthin, prasinoxanthin, heteroxanthin, vaucheriaxanthin, vaucherian xanthin ester, mixoxanthin, mixoxanthophyll, monadoxanthin, and lutein, phycobilin pigments exemplified by allophycocyanin, phycoerythrin, phycocyanin, and chlorophyll exemplified by chlorophyll (a, b, c1, c2, c3, and d), and perldinin, preferably, the above described catotenoid pigments, and more preferably astaxanthin, violaxanthin, echinenon, carotene, canthaxanthin, zeaxanthin, neoxanthin, and lutein, and particularly preferably astaxanthin, canthaxanthin, zeaxanthin, and the like.

As algae suitable for production of photosynthetic pigments, among algal species capable of the above described high density cultivation of algal cells, algal species mainly produce photosynthetic pigments are preferable. Specifically, it has been known that for example, the Cyanophycae of the Cyanophyta contains chlorophyll a, c-phycocyanin, c-phycoerythrin, allophycocyanin, β-carotene, echinenon, zeaxanthin, canthaxanthin, mixoxanthin, mixoxanthophyll, and oscillaxanthin, the prokaryotic chlorophyceae of the prokaryotic Chlorophyta contains chlorophyll (a and b), β-carotene, and zeaxanthin, the Glaucophyceae of the Glaucophyta contains chlorophyll a, phycocyanin, allophycocyanin, β-carotene, zeaxanthin, and cryptoxanthin, the Rhodophyceae of the Rhodophyta contains chlorophyll a, r-phycocyanin, and c-phycocyanin, r-phycoerythriene, and b-phycoerythriene, allophycocyanin, α- and β-carotene, lutein, violaxanthin, zeaxanthin, antheraxanthin, and neoxanthin, the Cryptophyceaee of the Cryptophyta contains chlorophyll (a and c2), α- and β-carotene, phycocyanin, phycoerythrin, alloxanthin, chloroxanthin, zeaxanthin, and monadoxanthin, the Dinophypceae of the Dinophyta (Pyrrophyta) contains chlorophyll (a and c2), β-carotene, peridinin, dinoxanthin, and diatoxanthin, the Crysophyceae of the Heterokontophyta (Chromphyta) contains chlorophyll (a, c1, c2, and c3), β-carotene, zeaxanthin, cryptoxanthin, anthetaxanthin, violaxanthin, fucoxanthin, neofucoxanthin, diatoxanthin, diadinoxantkin, and neoxanthin, the Xanthophyceae contains chlorophyll (a, c1, and c2), β-carotene, vaucheriaxanthin, diatoxanthin, heteroxanthin, and neoxanthin, the Eustigmatophyceae contains chlorophyll a, β-carotene, canthaxanthin, antheraxanthin, violaxanthin, vaucheriaxanthin, and neoxanthin, the Raphidophyceae contains chlorophyll (a, c1, and c2), β-carotene, diadinoxanthin, vaucheriaxanthin, heteroxanthin, dinoxanthin, neoxanthin, fucoxanthin, zeaxanthin, and violaxanthin, the Bacillariophyceae contains chlorophyll (a, c1, c2, and c3), β-carotene, echinenon, canthaxanthin, fucoxanthin, neofucoxanthin, diatoxanthin, diadinoxanthin, and neoxanthin, the Phaeophyceae contains chlorophyll (a, c1, c2, and c3), β-carotene, antheraxanthin, violaxanthin, fucoxanthin, diatoxanthin, diadinoxanthin, and neoxanthin, the Haptophyceae (Prymnesiophyceae) of the Haptophyta (Prymnesiophyta) contains chlorophyll (a, c1, and c2), α- and β-carotene, fucoxanthin, echinenon, canthaxanthin, diatoxanthin, diadinoxanthin, and dinoxanthin, the Euglenophyceae of the Euglenophyta Contains chlorophyll a and b, β-carotene, zeaxanthin, echinenon, diadinoxanthin, and neoxanthin, the Chlorarachniophyceae of the Chlorarachniophyta contains chlorophyll (a and b), β-carotene, zeaxanthin, echinenon, diadinoxanthin, and neoxanthin, the Chlorophyceae (in a wide sense) of the Chlorophyta contains chlorophyll (a and b), α-, β-, and γ-carotene, zeaxanthin, lutein, antheraxanthin, violaxanthin, neoxanthin, siphonein (chlorophyll found from some species of the order Siphonales), and sliphonaxanthin, and the Prasinophyceae contains chlorophyll (a and b), α- and β-carotene, prasinoxanthin, siphonein, and siphonaxantnin, and the Pedinophyceae contains chlorophyll (a and b).

Photosynthetic pigments contained by the above described various algal species can be produced in a high yield and a high purity by cultivating in the proper culture solution by using the inventors' cultivation apparatus for algae.

Algal species, which produce astaxanthin, used in the present invention are preferably exemplified by *Haematococcus pulvialis, Haematococcus lacustris*, green algae, belonging to Chlorococcum such as chlorella species exemplified by *Chlorella fusca, Chlorella zofingiensis, Chlorella homospphaera* and Scenedesmus species.

Algal species producing β-carotene and zeaxanthin are exemplified by *Spirulina platensis, Spirulina maxima, Spirulina subsalsa*, and more preferably *Spirulina platensis*.

Regarding condition of culture solution for production of astaxanthin, it has been known that green algae such as Haematococcus produces astaxanthin (2 mg/g) under an environment lacking a nutrient such as nitrogen deficiency.

Photosynthetic pigments can be produced by algae through cyst formation and pigmentation. Conditions of cyst formation and pigmentation are as follows. (1) Increasing light intensity. For example, intense light (50000 to 150000 lx). (2) Making $PO_4$-P in the culture solution deficient. (3) Making N (nitrogen) such as $NO_3$-N in the culture solution deficient (0 ppm). (4) Increasing the temperature of the culture (Raising the temperature for cultivation of a vegetative cell for about 10° C. from 20 to 28° C. Preferably the temperature is set to 30 to 35° C.). (5) Adding activated oxygen-generating agent (hydrogen peroxide $H_2O_2$, ozone $O_3$). (6) Salt stress (0.5% to 0.8% NaCl is added to the culture solution). (7) Sulphate starvation by removing $MgSO_4$, contained in the culture solution, or replacing to $MgCl_2$. (8) Adding a cell division inhibitor, for example, addition of Vinblastine to act as the cell division inhibitor yields an increased amount of astaxanthin.

According to the present invention, applying any one of respective conditions of the above described cyst formation and pigmentation or preferably, combination of two or three methods will make expect a further effect. For example, a combination of increasing light intensity, starvation of N and starvation of $PO_4$ can be exemplified as the preferable example.

In addition, it has been known that Chlorella and Scenedesmus, genera of green algae, produce astaxanthin (1.5 mg) by cultivation under the condition of N starvation and magnesium starvation. Further, the following report has been published: Chlorella and Scenedesmus, genera of green algae, having ability of astaxanthin biosynthesis cultivated in the culture solution containing 0.2 to 1 M of one or more kinds of a sodium salt and a potassium salt to produce green algae containing a high content (4 to 10 mg/g) of astaxanthin.

Algal species suitable for collection of photosynthetic pigments are exemplified by Chlorella, Spirulina, Dunaliella, Nannochloropsis (for example, *Nannochloropsis Oculata*), Thraustochytrium (for example, *Thraustochytrium aureum*), Crypthecodinium (for example, *Crypthecodinium Cohnii*), Isochrysis (*Isochrysis galbana*).

Dunaliella (genus Dunaliella of the Volvocales of the Chlorophyceae) contains abundant beta carotene in algal cells and preferably, *Dunaliella salina, Dunaliella bardawil*, and *Dunaliella tertiolecta*.

By algal cultivation employing the cultivation apparatus A of the present invention, a polysaccharide useful for medical drug material can be efficiently manufactured.

Polysacharlde in the sense of the present invention is water insoluble or water soluble polysaccharide of a molecular weight of ten thousands or higher, specifically, homoglycan (simple polysaccharide) consisting of a single monosaccharide and heteroglycan (complex polysaccharide) consisting of two or more monosaccharides. Homoglycan are exemplified by glucans such as cellulose, starch, glycogen, charonin, laminaran, and dextran, fructans such as inulin and levan, mannans, xylans, galacturonan such as pectin, mannuronans such as alginic acid, and N-acetyl glucosamine polymers such as chitin and heteroglycan are exemplified by guaran, mannan, heparin, chondroitin sulfuric acid, diheteroglycans such as hyaluronic acid, fucoidan, and agarose and are yielded by cultivation of algae.

Examples of usefulness of polysaccharides produced by algae are reported as a sulfated polysaccharide obtained from brown algae presents anticoagulating activity, blood purifying activity (lipoprotein lipase activity), and antitumor activity and fucosterol extracted from brown algae increases production of plasminogen activating factor in a vascular endothelial cell.

Algal polysaccharides are frequently used for health foods.

Algal species suitable for production of polysaccharides are exemplified by blue-green algae (cyanobacteria), red algae, haptophycean species, stigmatophycean species, xanthophycean species, bacillariophycean species, brown algae, green algae, and charophycean species.

Preferable genera are genus Chlorella such as Chlorella vulgaris and genus Nostoc such as Nostoc Commune.

Regarding the method for separating polysaccharides, a polysaccharide can be yielded by the method of extracting the polysaccharide from algae cultivated in the usual way, for example, breaking algal cells separated from the culture solution followed by an enzymatic reaction. In addition, when required, after cell breaking, fat-soluble components in cells are treated with a water-miscible organic solvent and remove the components to extract the polysaccharide.

The method for manufacturing algae containing photosynthetic pigments employing the cultivation apparatus A will be described below.

The culture solution, according to the present invention, for algal cells containing photosynthetic pigments can be those of publicly known or those after publicly known methods. The high density cultivation of algal cells containing photosynthetic pigments includes various types, cannot be restricted, and varies according to the structure of the cultivation apparatus, the volume of the cultivation apparatus, species of the alga used the initial density of algal cells, the kind of the culture solution, the composition of the culture solution, the pH of the culture solution, the temperature of cultivation, the light quantity irradiated on the cultivation container, irradiation time, duration of cultivation, the composition in aeration (air and the mixture gas of air and carbon dioxide), the aeration rate, the method for cyst formation, presence or absence of the additive such as a plant growth hormone regulating growth of the plant, presence or absence of the scavenger for removal of activated oxygen, and the like; however, normally, cultivation is conducted in the cultivation density ranging from 1 g to 10 g/L, preferably from 3 g to 10 g/L, and more preferably from 5 g to 10 g/L, and content of photosynthetic pigments yielded as a dry matter ranges from 0.8% to 9%, preferably from 4% to 9%, and more preferably from 7% to 9%.

Cultivation media usable are water, the artificial medium, natural freshwater, brackish water, and seawater, and those prepared by diluting these. Marine algae have am advantage, for example, that deep water available in the state of a low temperature, eutrophic, and axenic can be used as it is or regulating the temperature by using deep water with the low temperature for cultivation. In addition, appropriate dilution of deep water is usable for preparation of the culture solution. Further, when required, potassium nitrate, disodium phosphate, dipotassium phosphate, boric acid, magnesium chloride, manganese chloride, sodium molybdate, zinc sulfate, copper sulfate, and iron sulfate can be added.

Using the cultivation apparatus A, these algae can be cultivated in the high density and the high light-using efficiency.

The temperature of cultivation varies according to the species of algae to be cultivated and cannot be restricted; however, normally ranges from 15° C. to 35° C., preferably from 20° C. to 30° C., and more preferably from 20° C. to 25° C.

Sunshine amount (light amount) varies according to the species of algae used and cannot be restricted; however, normally ranges from 500 to 100000 lx, preferably from 5000 to 100000 lx, and more preferably 75000 to 100000 lx.

For accumulation of photosynthetic pigment such as astaxanthin in the high concentration requires a strong light; however, cultivation of for green algal cell, not so strong light is required.

Duration time for cultivation varies according to the species of algae cultivated, the temperature for cultivation, and sunshine amount (light amount), and cannot be restricted; however, normally ranges from 7 to 14 days and preferably about 10 days. In contrast, when by the conventional Spirulina cultivation method, the same amount as that of cultivation method according to the present invention is manufactured, one week to several weeks, normally, are necessary and hence, it can be known that the method for manufacture according to the present invention is distinctly improved in duration time.

For the method for cultivating algae containing photosynthetic pigments employing the cultivation apparatus A, a publicly known method for increasing content of photosynthetic pigments can be used. For example, in order to improve ability of astaxanthin production, the method, by which a green algal species. Haematococcus pulvialis, is cultivated at a high temperature for accumulation of a large amount of astaxanthin, can be applied. According to this method, when the above described algal is cultivated at 30° C., astaxanthin production becomes three times that at 20° C. and then, if acetic acid is supplied, carotenoid of the amount twice that produced without supply thereof is synthesized (Tjahjono A. E. et al., Biotechnol Lett. Vol. 16, No. 2. pp. 133–138. 1994).

In the case where the cultivation apparatus A was employed under the above described cultivation condition, not only increase in biomass, but also increase in accumulated amount of astaxanthin was found in algal cells.

Photosynthetic pigments yielded by the method for manufacture according to the present invention can be, after the usual way, isolated by filtering and centrifugation of algal cells contained in the culture medium, washed, and dried, and when required, algal cells are broken in the usual way and then, extracted by using a proper organic solvent for example a solvent such as methanol, ethanol, and acetone, which have a high polarity, or in combination of any one of these solvents with hexane and methylene chloride followed by separation and purification by silica gel column chromatography and HPLC or the like.

The method for collecting objective photosynthetic pigments from algal cells is not specially restricted, but the publicly known method can be followed. As the method for collecting efficiently objective photosynthetic pigments from algal cells, the following method, for example, can be applied (Japanese Patent Application Laid-Open No. 3-83577): Algal cells of high astaxanthin content are harvested from the culture solution and mechanically pulverized with glass beads of a particle size ranging from 0.25 to 5.0 mm under conditions of a sample density ranging from 0.1 to 10 weight % for 5 to 60 minutes treatment time.

For extraction of carotenoid pigments (photosynthetic pigments) from algae, the following method is applicable, for example: A cell wall of Haematococcus pulvialis alga is put under a high pressure to break by a turbulent flow followed by drying for extraction with the organic solvent to yield the astaxanthin carotenoid pigment. For extraction after algal cell wall break, in the usual way, the above described proper organic solvent can be used for extraction.

The third of the present invention is a method for manufacturing algal cells containing highly unsaturated fatty acids by the high density cultivation method for algae producible of highly unsaturated fatty acids employing the cultivation apparatus A.

The high density cultivation method for algal cells containing highly unsaturated fatty acids includes various types, cannot be restricted, and varies according to the structure of the cultivation apparatus, the volume of the cultivation apparatus, species of the alga used, the initial cultivation density of algae, the kind of the culture solution, the composition of the culture solution, the pH of the culture solution, the temperature of cultivation, the light quantity irradiated on the cultivation container, irradiation time, duration of cultivation, the composition in aeration (air and the mixture gas of air and carbon dioxide), the aeration rate, presence or absence of the additive such as a plant growth hormone regulating growth of the plant, presence or absence of the scavenger for removal of activated oxygen, or the like; however, normally, cultivation is conducted in the cultivation density ranging from 1 g to 10 g/L, preferably from 3 g to 10 g/L, and more preferably from 5 g to 10 g/L, and content of highly unsaturated fatty acids yielded as the dry matter ranges from 0.8% to 9%, preferably from 4% to 9%, and more preferably from 7% to 9%.

Highly unsaturated fatty acids yielded by the high density cultivation for algae according to the present invention is not specially restricted; however, normally represent fatty acids consisting of 18 to 22 carbon atoms having 4 to 6 unsaturated bonds. Specifically, examples are docosahexaenoic acid (DHA) having 6 unsaturated bonds and consisting 22 carbon atoms, eicosapentaenoic acid (EPA) having 5 unsaturated bonds and consisting of 20 carbon atoms, and arachidonic acid (ARA) having 4 unsaturated bonds and consisting of 20 carbon atoms.

As usefulness of highly unsaturated fatty acids, for example, DHA and ester thereof, as effective constituents, have been reported as application to a cerebral function enhancer (Japanese Patent Application Laid-Open No. 1-153629), a composition of a cerebral function improving agent, a learning ability enhancer, a memory enhancer, a dementia preventive agent, a dementia remedy, or a functional food having a cerebral function improving effect (Japanese Patent Application Laid-Open No. 2-49723).

As conventional methods for manufacturing highly unsaturated fatty acids, the following methods have been reported.

The method for manufacturing highly unsaturated fatty acids (DHA) by conversion reaction using Mortierella species (Japanese Patent Application Laid-Open No. 63-185389), the method for manufacturing a fat containing highly unsaturated fatty acids of an amount increased by a microbe capable of producing arachidonic acid (Japanese Patent Application Laid-Open No. 1-304892), the method for manufacturing a lipoid containing highly unsaturated fatty acids derived from marine microbes (Japanese Patent Application Laid-Open No. 2-142486), the method for manufacturing highly unsaturated fatty acids by a species of Echinosporangium (Japanese Patent Application Laid-Open No. 2-23878), the method for obtaining highly unsaturated fatty acids from the culture of Echinosporangium Transversalie ATCC 16960 and 18036 (European published unexamined application 35597), and a bacterium, a fungus Thraustochytrium, Entomophthora, Japonochytrium sp. ATCC 28207 (Japanese Patent Application Laid-Open No. 1-199588).

The method for obtaining DHA by cultivation of algae, methods for cultivating Dinophycean algae and Haptophycean algae have been reported (Joseph, J. D.: Lipids, 10, 395 (1975), Nichols, P. D. et al.; Phytochemistry 23: 1043 (1984)).

However, the above described are a natural propagation method or a simple still cultivation method and therefore, have technical problems for industrial practice.

As algal species preferable to manufacture of algae containing highly unsaturated fatty acids by the high density cultivation by employing the cultivation apparatus A according to the present invention, algal species producible of highly unsaturated fatty acids can be freely chosen from the above described algal species.

Specifically, *Isochrysis galvana* producible of highly unsaturated fatty acids (DHA) and *Nannochloropsis oculata* and *Monodus subterraneus*, which are producible of highly unsaturated fatty acids (EPA), can be exemplified. In the high density cultivation method according to the present invention, any one or two or more species of the above described algae can be combined for use.

The above described *Isochrysis Galbana* belongs to the Haptophyceae, which is marine microalgal group. In addition, *Chaetoceros Gracilis* and *Chaetoceros Calcitrans* belonging to the genus Chaetoceros, Cryptomonas sp. belonging to Cryptomonas, and as well, *Pavlova Lutheri* and *Cricosphaere Carterae* are also preferable.

*Isochrysis galbana* is specifically exemplified by *Isochrysis galbana* LB2307 and LB9807, *Chaetoceros gracilis* is specifically exemplified by 2375, *Chaetoceros calcitrans* is specifically exemplified by CCAL1315, Cryptomonas sp. is specifically exemplified by LB2423, *Pavlova lutheri* is specifically exemplified by LB1293, and *Cricosphaere carterae* is specifically exemplified by LB1014 and LB2167. These algal species can be used in combination of one or two or more species for mixture.

In the case where highly unsaturated fatty acid is EPA, for example, unicellular alga Monodus, Eustigmatopceae species, and *Nannochloropsis oculata* that are planktonic and containing abundant EPA, are preferable.

Cultivation condition is of the method following the manufacturing method of algal cells (biomass) as described above.

According to the present invention, by employing the cultivation apparatus A as a simple method, a light environment in the culture solution can be made optimal and thus, the cultivation rate can be further enhanced by continued irradiation and intermittent irradiation.

According to the present invention, by the high density cultivation, algae can be produced in the high purity and a high yield. In addition, when required, the culture solution can received a publicly known plant hormone such as auxin, gibberellin, and cytokinin to enhance growth of algae such as Euglena.

Highly unsaturated fatty acids yielded by the method for manufacture according to the present invention can be, after the usual way, isolated by filtering and centrifugation of algal cells contained in the culture medium, washed, and dried, and when required, algal cells are broken in the usual way and then, extracted by using the proper organic solvent, for example a solvent such as ethanol, methanol, ethanol, and acetone, which have the high polarity, or in combination of any one of these solvents with hexane and methylene chloride followed by separation and purification by silica gel column chromatography and HPLC and the like.

EXAMPLES

Example 1

*Isochrysis Galbana* Producible of DHA

Using the cultivation apparatus A, an algal species, *Isochrysis Galbana* was cultured in the initial algal cultivation density (0.3 g/L) and under the following conditions: the volume of the culture was 120 liter, the composition of the culture solution is presented in Table 1, the temperature of cultivation ranged 15° C. to 25° C., the sunlight quantity and sunshine time were 14.3 MJ and 12.5 hours, the aeration rate of the mixture gas of air and carbon dioxide,(carbon dioxide concentration 2.0%) was 30 liter/minute, the pH of the culture solution was 7.0 to 8.0, and culture period was 10 days.

As a result, high content algal cells (biomass) containing highly unsaturated fatty acids (DHA) of 8% dry matter could be yielded through the culture density of 10.0 g/L.

Composition of Culture Medium

TABLE 1

| Name of component | Amount used |
|---|---|
| NaCl | 35.1 g/L |
| $MgSO_4 \cdot 7H_2O$ | 6.6 g/L |
| $MgC_{12} \cdot 6H_2O$ | 5.6 g/L |
| $CaCl_4 \cdot 2H_2O$ | 1.5 g/L |
| $KNO_3$ | 1.0 g/L |
| $KH_2PO_4$ | 70 mg/L |
| Vitamins (1) | 1.0 ml/L |
| Trace elements (2) | 1.0 ml/L |
| Irons (3) | 1.0 ml/L |
| Water | 1 L |
| (1) Composition of vitamins | |
| Thiamine hydrochloride | 400 mg/L |
| Biotin | 100 mg/L |
| Vitamin $B_{12}$ | 10 mg/L |
| (2) Composition of trace elements | |
| $ZnSO_4 \cdot 7H_2O$ | 8.4 mg/L |
| $H_3BO_3$ | 60.0 mg/L |
| $CoCl_2 \cdot 6H_2O$ | 1.5 mg/L |
| $CuCl_2 \cdot 2H_2O$ | 4.0 mg/L |
| $MnCl_2 \cdot 4H_2O$ | 40.0 mg/L |
| $(NH_4)_6Mo_7O_{24} \cdot 4H_2O$ | 37.0 mg/L |
| (3) Composition of irons | |
| $Na_2EDTA$ | 18.60 mg/L |
| $FeCl_3 \cdot 4H_2O$ | 2.40 mg/L | pH: a range from 7.5 to 8.0 was applied.

Example 2

*Isochrysis Galbana* Producible of DHA

Using the present cultivation apparatus, under the culture condition of the example 1, $ZnCl_2$ in the composition of the culture medium was replaced to $ZnSO_4$-$7H_2O$ 8.4 mg/L, $FeCl_3$-$4H_2O$ was replaced to $FeCl_3$-$6H_2O$ 2.77 8/L to culture an algal species *Isochrysis Galbana*. As a result, high content algal cells (biomass) containing highly unsaturated fatty acids (DHA) of 7.5% dry matter could be yielded through the culture density of 5.0 g/L.

Example 3

Method for Manufacturing *Spirulina Platensis*

Using the present culture apparatus, the algal species, *Spirulina platensis* was cultured in the initial algal cultivation density (0.5 g/L) and under the following conditions: the volume of the culture was 120 liter, the composition of the culture solution is presented in Table 2, the temperature of cultivation ranged 25° C. to 35° C., the sunlight quantity and sunshine time were 18 MJ/m² and 14.5 hours, the aeration rate of the mixture gas of air and carbon dioxide (carbon dioxide concentration 2.0%) was 25 liter/minute, the pH of the culture solution was 8.5 to 10.0, and culture period was 10 days. As the result, productivity ranging 2.0 to 5.0 g/L/day could be realized through the culture density of 10 to 20 g/L.

In comparison with the conventional culture method as the comparative example 1 presented below, productivity was about 10 times.

TABLE 2

| Name of component | Amount used |
| --- | --- |
| NaCl | 1.00 g/L |
| NaNO$_3$ | 2.50 g/L |
| CaCl$_2$ | 0.04 g/L |
| FeSO$_4$ · 7H$_2$O | 0.01 g/L |
| Na$_2$EDTA | 0.08 g/L |
| K$_2$SO$_4$ | 1.00 g/L |
| MgSO$_4$ · 7H$_2$O | 0.20 g/L |
| KHPO$_4$ | 0.50 g/L |
| NaHCO$_3$ | 16.80 g/L |
| A-solution (1) | 1.00 ml/L |
| B-solution (2) | 1.00 ml/L |
| Water | 1 L |
| (1) Composition of A-solution | |
| ZnSO$_4$ · 7H$_2$O | 222 mg/L |
| CuSO$_4$ · 5H$_2$O | 79 mg/L |
| MoO$_3$ | 15 mg/L |
| H$_3$BO$_3$ | 2,860 mg/L |
| MnCl$_2$ · 2H$_2$O | 1,810 mg/L |
| (2) Composition of B-solution | |
| NH$_4$NO$_3$ | 23 mg/L |
| K$_2$Cr$_2$(SO$_4$)$_2$ · 24H$_2$O | 96 mg/L |
| NiSO$_4$ · 7H$_2$O | 48 mg/L |
| Na$_2$WO$_4$ · 2H$_2$O | 18 mg/L |
| Co(NO$_3$)$_2$ · 6H$_2$O | 44 mg/L |
| Ti$_2$(SO$_4$)$_3$ | |

Na$_2$EDTA presented in the above described Table shows disodium salt of EDTA.

Comparative Example 1

Conventional Culture Method (*Spirulina Platensis*)

Under the culture condition of the above described Example 1, the culture apparatus was replaced to a conventional cultivation pond system and then, culture density of *Spirulina platensis* was 0.3 to 0.5 g/Liter and productivity thereof was 0.1 to 0.2 g/L/day.

Example 4

Method for Manufacturing Astaxanthin by *Haematococcus Pulvialis*

Using the cultivation apparatus A, an algal species, *Haematococcus pulvialis* was cultured in the initial algal cultivation density (0.5 g/L) and under the following conditions: the volume of the culture was 80 liter, the composition of the culture solution is presented in Table 3, the temperature of cultivation ranged 25° C. to 30° C., the sunlight quantity and sunshine time were 17.5 MJ/m$^2$ and 13.5 hours, the aeration rate of the mixture gas of air and carbon dioxide (carbon dioxide concentration 2.0%) was 25 liter/minute, the pH of the culture solution was 7.5 to 8.5, and culture period was 10 days. Aeration was stopped, algal cells precipitated were collected, and the culture medium prepared by removing N and P from the above described culture medium was added to culture under string light for 4 days. As a result, high content algal cells (biomass) containing a pigment astaxanthin of 4% to 8% could be yielded through the high density culture in the culture density of 5 g to 10 g/L.

TABLE 3

| Name of component | Amount used |
| --- | --- |
| NaNO$_3$ | 1.50 g/L |
| CaCl$_2$ · 2H$_2$O | 0.036 g/L |
| Na$_2$CO$_3$ | 0.02 g/L |
| MgSO$_4$ · 7H$_2$O | 0.075 g/L |
| EDTA | 0.001 g/L |
| K$_2$HPO$_4$ | 0.039 g/L |
| Citric acid | 0.006 g/L |
| Ammonium citrate | 0.006 g/L |
| Iron A-solution (1) | 1.0 ml/L |
| PH:7.0 | |
| (1) Composition of A-solution | |
| ZnSO$_4$ · 7H$_2$O | 222 mg/L |
| CuSO$_4$ · 5H$_2$O | 79 mg/L |
| MoO$_3$ | 15 mg/L |
| H$_3$BO$_3$ | 2,860 mg/L |
| MnCl$_2$ · 2H$_2$O | 1,810 mg/L |

Comparative Example 2

Method for Culture of *Haematococcus Pulvialis*

Under the culture condition of the above described Example 4, the culture apparatus was replaced to a conventional cultivation pond system to culture *Haematococcus pulvialis*.

As a result, culture it was found that *Haematococcus pulvialis* itself was very difficult.

Example 5

Manufacture of EPA by Method for Culture of *Nannochloropsis Oculata*

Using the cultivation apparatus A, the algal species, *Nannochloropsis oculata*, a marine microalga, was cultured in the initial algal cultivation density (0.4 g/L) and under the following conditions: the volume of the culture was 120 liter, the composition of the culture solution is presented in a separate sheet 5, the temperature of cultivation ranged 25° C. to 30° C., the sunlight quantity and sunshine time were 16.3 MJ/m$^2$ and 13.5 hours, the aeration rate of the mixture gas of air and carbon dioxide (carbon dioxide concentration 2.0%) was 30 liter/minute, the pH of the culture solution was 7.0 to 8.0, and culture period was 10 days.

As a result, high content algal cells (biomass) containing highly unsaturated fatty acids (EPA) 10% of dry matter could be yielded through the high density culture of 8 g/L.

TABLE 4

| Name of component | Amount used |
| --- | --- |
| NaCl | 35.1 g/L |
| MgSO$_4$ · 7H$_2$O | 6.6 g/L |
| MgCl$_2$ · 6H$_2$O | 5.6 g/L |
| CaCl$_2$ · 2H$_2$O | 1.5 g/L |
| KNO$_3$ | 1.0 g/L |
| KH$_2$PO$_4$ | 70 mg/L |
| Vitamins (1) | 1.0 ml/L |
| Trace elements (2) | 1.0 ml/L |
| Irons (3) | 1.0 ml/L |
| Water | 1 L |
| (1) Composition of vitamins | |
| Thiamine hydrochloride | 400 mg |
| Biotin | 100 mg |

TABLE 4-continued

| Name of component | Amount used |
|---|---|
| Vitamin B$_{12}$ | 10 mg |
| (2) Composition of trace elements | |
| ZnSO$_4$ · 7H$_2$O | 4.0 mg/L |
| H$_3$BO$_3$ | 60.0 mg/L |
| CoCl$_2$ · 6H$_2$O | 1.5 mg/L |
| CuCl$_2$ · 2H$_2$O | 4.0 mg/L |
| MnCl$_2$ · 4H$_2$O | 40.0 mg/L |
| (NH$_4$)$_6$Mo$_7$O$_{24}$ · 4H$_2$O | 37.0 mg/L |
| (3) Composition of Irons | |
| Na$_2$EDTA | 18.60 g/L |
| FeCl$_3$ · 4H$_2$O | 2.40 g/L |
| PH:7.6 | |

Example 6

Manufacture of EPA by Method for Culture of *Nannochloropsis Oculata*

Using the cultivation apparatus A, *Nannochloropsis oculata* was cultured under the same culture condition as that of the example 5.

As a result, high content algal cells (biomass) containing highly unsaturated fatty acids (EPA) 8% of dry matter could be yielded through the high density culture of 3 g/L.

Comparative Example 3

Manufacture of EPA by Method for Culture of *Nannochloropsis Oculata*

Under the culture condition of the above described Example 5, the culture apparatus was replaced to a conventional cultivation pond system to culture *Nannochloropsis oculata*.

As a result, this manufacturing method showed a limit in the culture density of biomass ranging 0.2 to 0.4 g/L Example 7

Manufacture of ARA by Culture of a Snow Algal Species

Using the cultivation apparatus A, a snow algal species, *Paietochloris inciss*, was cultured in the initial algal cultivation density (0.5 g/L) and under the following conditions: the volume of the culture was 120 liter, the composition of the culture solution is presented in a Table 5, the temperature of cultivation ranged 25° C., the sunlight quantity was 15 MJ/m$^2$, the aeration rate of the mixture gas of air and carbon dioxide (carbon dioxide concentration 2.0%) was 30 liter/minute, the ph of the culture solution was 7, and culture period was two weeks. As a result, algal cells was cultured to a final biomass density of 0.5 g/L. Filtering and drying algal cells presented a yield containing arachidonic acid of 6.5 weight % (w/w %) dry weight. Amount of arachidonic acid (ARA) is the amount calculated by conversion of triarachidonyl glyceride, arachidonic acid monoester, and arachidonic acid diester, which are contained in algal cells, to arachidonic acid.

TABLE 5

| Name of component | Amount used |
|---|---|
| NaNO$_3$ | 20 g/L |
| MgSO$_4$ · 7H$_2$O | 0.075 g/L |
| NaCl | 0.025 g/L |

TABLE 5-continued

| Name of component | Amount used |
|---|---|
| K$_2$HPO$_4$ | 0.075 g/L |
| KH$_2$PO$_4$ | 0.175 g/L |
| CaCl$_2$ · 2H$_2$O | 0.025 g/L |
| Trace element solution | |
| ZnSO$_4$ · 7H$_2$O | 8.82 mg/L |
| MnCl$_2$ · 4H$_2$O | 1.44 mg/L |
| MoO$_3$ | 0.71 mg/L |
| CuSO$_4$ · 5H$_2$O | 1.57 mg/L |
| CoNO$_3$ · 6H$_2$O | 0.49 mg/L |
| H$_3$BO$_3$ | 11.42 mg/L |
| EDTA-KOH solution | |
| Na$_2$EDTA | 50 mg/L |
| KOH | 31 mg/L |
| FeSO$_4$ · 7H$_2$O | 4.98 mg/L |
| Conc. sulfuric acid | 0.001 ml |

Example 8

Using the cultivation apparatus A, a Nostoc species, *Nostoc commune*, was cultured in the initial algal cultivation density (0.5 g/L) and under the following conditions: the volume of the culture was 120 liter, the composition of the culture solution is presented in a Table 6, the temperature of cultivation ranged 25° C., the sunlight quantity was 7 to 10 MJ, the pH of the culture solution was 7.6 to 7.8, and culture period was two weeks.

As a result, algal cells yielded were of 4 to 5 g/L as the final biomass density.

The biomass obtained was extracted with hot water and yielded polysaccharide of 10 to 15% dry weight. As the result of analysis of polysaccharide extracted, 4% β-1,3-glucan was detected for dry weight.

TABLE 6

| Name of component | Amount used |
|---|---|
| K$_2$HPO$_4$ | 0.04 g/L |
| MgSO$_4$ · 7H$_2$O | 0.075 g/L |
| CaCl$_2$ · 2H$_2$O | 0.036 g/L |
| Citric acid | 0.006 g/L |
| Ammonium citrate green | 0.006 g/L |
| Na$_2$EDTA | 0.001 g/L |
| Na$_2$CO$_3$ | 0.02 g/L |
| Stock solution | 1.0 mL |

The stock solution is shown in the following Table 7.

TABLE 7

| Name of component of stock solution | Amount used |
|---|---|
| H$_3$BO$_3$ | 2.86 g/L |
| MnCl$_2$ · 4H$_2$O | 1.81 g/L |
| ZnSO$_4$ · 7H$_2$O | 0.22 g/L |
| Na$_2$MoO$_4$ · 2H$_2$O | 0.89 g/L |
| CuSO$_4$ · 5H$_2$O | 0.08 g/L |
| CoNO$_3$ · 6H$_2$O | |

Algal species of the genus Nannochloropsis, for example, *Nannochloropsis oculata* is useful for reproduction of Rotifera species used as a feed for young fish in culture.

Algae belonging to the genus Phaeodactylum, for example, *Phaeodactylum tricornutum*, species of the genus Chaetoceros, for example, *Chaetoceros gracilis* is famous as the feed for bivalves, abalone, and crustaceans such as shrimp. In natural world, increase and decrease (tide) of these algae depend on change of seasons and environment and therefore, so far, such change of algal biomass was compensated by cultivation in the open pond. However, the open pond is influenced by change of natural environment and thus, algal cells were not stably supplied and also efficient production of a necessary target species was difficult.

By using the biodome of a closed type, algae of the high quality can be produced and supplied stably.

Example 9

Using the cultivation apparatus A, *Phaeodactylum tricornutum*, was cultured in the initial algal cultivation density (0.3 g/L) and under the following conditions: the volume of the culture was 120 liter, the composition of the culture solution (artificial seawater) is presented in a Table 8, the temperature of cultivation ranged 26 C, the light intensity was 5 MJ, the pH of the culture solution was 7.5 to 8.5, and culture period was two weeks.

As a result, algal cells yielded were of 5 g/L as the final biomass density.

The biomass obtained was used as the feed in mariculture (feed for feed).

TABLE 8

| Name of component of artificial seawater | Per 1 liter |
| --- | --- |
| Stock solution 1 | 8.75 mL |
| Stock solution 2 | 2.5 mL |
| Table Salt | 88.6 g |
| Soil extract | 25.0 g |
| Tricin | 0.5 g |

In the Table, compositions of Stock solution 1 and Stock solution 2 are presented in Table 9 and Table 10.

TABLE 9

| Name of component of Stock solution 1 | Amount used |
| --- | --- |
| $NaNO_3$ | 30.0 g/L |
| $Na_2HPO_4$ | 1.2 g/L |
| $K_2HPO_4$ | 1.0 g/L |

TABLE 10

| Name of component of Stock solution 2 | Amount used |
| --- | --- |
| Biotin | 0.0002 g/L |
| Calcium pantothenate | 0.02 g/L |
| Cyanocobalamin | 0.004 g/L |
| Folic acid | 1.0 g/L |
| Inositol | 1.0 g/L |
| Nicotinic acid | 0.02 g/L |
| Thiamine hydrochloride | 0.1 g/L |
| Thymine | 0.6 g/L |

Effect of the Invention

Using the inventors' cultivation apparatus provides the method for obtaining algal cells (biomass) in the high purity and high yield. In addition, the biomass yielded can provide algal cells containing photosynthetic pigments and/or highly unsaturated fatty acids and/or polysaccharides in the high concentration. Therefore, the comparatively simple apparatus allows manufacturing readily photosynthetic pigment and/or highly unsaturated fatty acids and/or polysaccharides.

What is claimed is:

1. A method for culturing algae, which has ability of producing a highly unsaturated fatty acid, and/or a photosynthetic pigment, and/or a polysaccharide, in a high density in a medium, the method comprising the step of:

cultivating algae in a cultivation apparatus under light irradiation and aeration conditions to manufacture the algae containing the highly unsaturated fatty acid, and/or the photosynthetic pigment, and/or the polysaccharide, wherein said cultivation apparatus is that selected from those with any one shape of a dome shape, a conical shape, or a cylindrical shape;

the cultivation apparatus with the dome shape comprises an external hemispheric dome made from a clear material, an internal hemispheric dome made from the clear material, and a bottom part connecting bottom end parts of both the domes, and a cylindrical opening member is installed on a top part of the external hemispheric dome and a leading member for air and/or carbon dioxide gas and a discharging member for the culture solution are installed on the bottom part;

the cultivation apparatus with the conical shape comprises an external conical circumferential wall made of the clear material, a clear internal conical circumferential wall, and a bottom part connecting bottom end parts of both the circumferential walls, and a cylindrical opening member is installed on the top part of the external conical circumferential wall and a leading member for air and/or carbon dioxide gas and a discharging member for the culture solution are installed on the bottom part;

or, the cultivation apparatus with the cylindrical shape comprises an external cylindrical circumferential wall having an upper wall made of the clear material, an internal cylindrical circumferential wall having an upper wall made of the clear material, and a bottom part connecting bottom end parts of both the circumferential walls, and a cylindrical opening member is installed on a central part of the upper wall of the external cylindrical circumferential wall and a leading member for air and/or carbon dioxide gas and a discharging member for the culture solution are installed on the bottom part.

2. The method according to claim 1, wherein said clear material is at least one material selected from an acrylic resin, polycarbonate, polypropylene, polyethylene, and polyvinyl chloride.

3. The method according to claim 1, wherein in said cultivation apparatus the outside of the cylindrical opening member of the cultivation apparatus has further a water spraying member and an outer circumference of the bottom part has a water spray-receiving member.

4. The method according to claim 1, wherein said step of cultivating algae in a cultivation apparatus comprises continuous cultivation in the cultivation apparatus in which an artificial light source is further installed in the internal hemispheric dome and an inside space of the internal conical circumferential wall or the internal cylindrical circumferential wall of the cultivation apparatus.

5. A method for culturing algae, which has ability of producing the highly unsaturated fatty acid, and/or the photosynthetic pigment, and/or the polysaccharide, in the high concentration in the medium, said method comprising the step of:
cultivating algae in a cultivation apparatus under light irradiation and aeration conditions to manufacture the algae abundantly containing the highly saturated fatty acid, and/or the photosynthetic pigment, and/or the polysaccharide, wherein said cultivation apparatus comprises a main body of the cultivation apparatus and a gas discharging apparatus; and the main body of the cultivation apparatus is the cultivation apparatus with a dome shape, conical shape, or cylindrical shape, wherein the cultivation apparatus with the dome shape comprises an external hemispheric dome made from a clear material, an the internal hemispheric dome made from the clear material, and a bottom part connecting bottom parts of both the domes, and a cylindrical opening member is installed on the top part of the external hemispheric dome and the discharging apparatus for the culture solution is installed on the bottom part;

the cultivation apparatus with the conical shape comprises an external conical circumferential wall made of the clear material, an internal conical circumferential wall made from the clear material, and a bottom part connecting bottom end parts of both the circumferential walls, and a cylindrical opening member is installed on the top part of the external conical circumferential wall and the discharging apparatus for the culture solution is installed on the bottom part;

or, the cultivation apparatus with the cylindrical shape comprises an external cylindrical circumferential wall having an upper wall made of the clear material, an internal cylindrical circumferential wall having an upper wall made of the clear material, and a bottom part connecting bottom end parts of both the circumferential walls, and a cylindrical opening member is installed on the central part of the upper wall of the external cylindrical circumferential wall and the discharging apparatus for the culture solution is installed on the bottom part;

the gas discharging apparatus is configured by opposite two square base boards, a bubble leading member, of which section has a square shape lacking a side or a reversed U-shape, opened downward, and a discharge nozzle, the bubble leading member is installed with inclination to an upper side face of the square base board, forms the upper wall made by extending an inclined wall of the upper face of the bubble leading member by bending almost horizontally in the upper end part, and has a side wall extending from both the side ends of the inclined wall and the upper wall, and each of the bottom end parts of both the side walls are jointed on the two upper side faces of the square based board, and the discharge nozzle is rotatably attached through a via hole made in the bottom part of the inclined wall.

6. The method according to claim 5, the clear material consisting of the main body of the cultivation apparatus is one or more material selected from the acrylic resin, polycarbonate, polypropylene, polyethylene, and polyvinyl chloride.

7. The method according to claim 5, wherein said cultivation apparatus comprises a water spraying member further installed in outside of the cylindrical opening member and a water spray receiving member further installed in the outer circumference of the bottom part of the main body of the cultivation apparatus.

8. The method according to claim 5, wherein said cultivating step comprises continuous cultivation in the cultivation apparatus in which an artificial light source is further installed in the internal hemispheric dome and the inside space of the internal conical circumferential wall or the internal cylindrical circumferential wall of the cultivation apparatus.

9. The method according to claim 5, wherein in said cultivation apparatus, the gas discharge apparatus for air and/or carbon dioxide gas is further installed on the bottom part of the main body of the cultivation apparatus.

10. The method according to claim 5, wherein said cultivation apparatus further comprises the gas discharge apparatus in which at least any one of the square base boards thereof is bent to a same direction in a front end part and/or a rear end part and/or a rear end part.

11. The method according to claim 5, wherein said cultivation apparatus further comprises the gas discharge apparatus in which at least any one of two square base boards thereof has weight-adjusting means.

* * * * *